United States Patent
Humphrey

(10) Patent No.: US 6,171,239 B1
(45) Date of Patent: Jan. 9, 2001

(54) SYSTEMS, METHODS, AND DEVICES FOR CONTROLLING EXTERNAL DEVICES BY SIGNALS DERIVED DIRECTLY FROM THE NERVOUS SYSTEM

(75) Inventor: Donald R. Humphrey, Atlanta, GA (US)

(73) Assignee: Emory University, Atlanta, GA (US)

(*) Notice: Under 35 U.S.C. 154(b), the term of this patent shall be extended for 0 days.

(21) Appl. No.: 09/135,249

(22) Filed: Aug. 17, 1998

(51) Int. Cl.⁷ .................................................. A61B 5/04
(52) U.S. Cl. ........................ 600/372; 600/378; 600/544; 607/116
(58) Field of Search ................................... 600/372, 373, 600/377, 378, 383, 544, 545; 607/116, 117, 118, 62; 606/129, 130

(56) References Cited

U.S. PATENT DOCUMENTS

| | | |
|---|---|---|
| 3,718,134 | 2/1973 | Brindley . |
| 3,722,005 | 3/1973 | Cowland . |
| 4,026,300 | 5/1977 | DeLuca et al. . |
| 4,030,141 | 6/1977 | Graupe . |
| 4,031,882 | 6/1977 | DeLuca . |
| 4,046,141 | 9/1977 | DeLuca . |
| 4,140,997 * | 2/1979 | Brady ................................... 600/545 |
| 4,158,196 | 6/1979 | Crawford, Jr. . |
| 4,314,379 | 2/1982 | Tanie et al. . |
| 4,461,304 * | 7/1984 | Kuperstein ........................... 600/378 |
| 4,558,704 | 12/1985 | Petrofsky . |
| 4,685,925 | 8/1987 | Childress et al. . |
| 4,852,573 | 8/1989 | Kennedy . |
| 4,964,061 | 10/1990 | Grodski et al. . |
| 5,037,376 | 8/1991 | Richmond et al. . |
| 5,062,857 | 11/1991 | Berringer et al. . |
| 5,167,229 | 12/1992 | Peckham et al. . |

(List continued on next page.)

OTHER PUBLICATIONS

Asanuma and Arissian, "Motor deficits following interruption of sensory inputs to the motor cortex of the monkey," *Kyoto Symposia (EEG Suppl.,* 36) 415–21 (1982) (Editors: P.A. Buser, et al., Elsevier Biomedical Press, Amsterdam).*

Burrow, et al., "Cortical control of an alpha II robot arm," *Proc. Int. Conf. IEEE Eng. Med. Biol.,* 4:1479–1480 (1992).*

Burrow, et al., "Cortical control of a robotic manipulator," *Proc. Int. Conf. Rehab. Robot.,* 74–86 (1992) (Published by the Applied Science and Engineering Laboratory, A. I. Dupont Institute; University of Delaware Press).*

(List continued on next page.)

Primary Examiner—Linda C. M. Dvorak
Assistant Examiner—David M. Ruddy
(74) Attorney, Agent, or Firm—James L. Ewing, IV; Geoff L. Sutcliffe; Kilpatrick Stockton LLP

(57) ABSTRACT

A system and method control prostheses and other devices with signals received by sensors implanted directly in the brain or other parts of the nervous system of a subject/patient and transmitted to an external receiver. Included in the system are sensors in the form of bundles of small, insulated, flexible wires, configured in a parallel or twisted array, which are used to receive multicellular signals from small clusters of neurons. A new "calibration/adaptation" system is developed, in which the neural signals are cross-correlated with the parameters of a set of standardized or model movements as the subject/patient attempts to emulate the model movements, and on the basis of the correlations the neural signals that are best suited for control of the corresponding movement or movement parameter of the external device are selected. Periodic use of this calibration system compensates for or adapts to uncontrolled changes in neural signal parameters over time, and therefore results in re-selection of the optimal neural channels for better device control. Artificial neural nets are used for mapping the selected neural signals onto appropriate movements or control parameters of the external device.

42 Claims, 13 Drawing Sheets

U.S. PATENT DOCUMENTS

| | | | |
|---|---|---|---|
| 5,178,161 | * | 1/1993 | Kovacs ................................. 600/378 |
| 5,215,088 | | 6/1993 | Normann et al. . |
| 5,279,305 | | 1/1994 | Zimmerman et al. . |
| 5,336,269 | | 8/1994 | Smits . |
| 5,376,128 | | 12/1994 | Bozeman, Jr. . |
| 5,413,103 | | 5/1995 | Eckhorn . |
| 5,496,369 | | 3/1996 | Howard, III . |
| 5,524,338 | | 6/1996 | Martyniuk et al. . |
| 5,617,515 | | 4/1997 | MacLaren et al. . |
| 5,638,826 | | 6/1997 | Wolpaw et al. . |
| 5,692,517 | | 12/1997 | Junker . |
| 5,710,870 | | 1/1998 | Ohm et al. . |
| 5,735,887 | * | 4/1998 | Barreras, Sr. et al. ................ 607/60 |
| 5,748,845 | | 5/1998 | Labun et al. . |
| 5,859,934 | | 1/1999 | Green . |
| 5,928,143 | * | 7/1999 | McNaughton ....................... 600/373 |
| 5,935,078 | * | 8/1999 | Feierbach ........................... 600/509 |
| 5,983,128 | * | 11/1999 | Baudonniere et al. .............. 600/544 |

OTHER PUBLICATIONS

Burrow, et al., "The development of a neurological interface using quadratic distance decision and neural network pattern recognition techniques," *Prof. Int. Conf. Rehabil. Robot.* 4:195–200 (1994).*

Carpenter, *Core Text of Neuroanatomy*, 2nd Edition, Table of Contents, Baltimore, Maryland (Williams & Williams, Baltimore/London) (1978).*

Cohen, et al., "Topographic maps of human motor cortex in normal and pathological conditions: mirror movements, amputations, and spinal cord injuries," *Magnetic Motor Stimulation: Basic Principles and Clinical Experience (EEG Supplement. 43)* 36–50 (1991) (Editors: W. J. Levy, et al., Elsevier Science Publishers, B.V.).*

Deiber, et al., "Distinct cerebral activity in imagination and execution of movement," *Soc. Neurosci Abstr.*, 21:1421 (1995).*

Donoghue, et al., "Organzation of the forelimb area in squirrel monkey primary motor cortex: representation of individual digit, wrist, and elbow muscles," *Exp. Brain Res.*, 89:1–19 (1992).*

Donoghue and Sanes, "Motor areas of the cerebral cortex," *J. Clin. Neurophysiol.*, 11(4):382–396 (1994).*

Echard, et al., "Viability of quadratic distance decisions for use in pattern recognition," *Proc. South. Biomed. Eng. Conf.*, 11:153–156 (1992).*

Evarts, E.V., "Pyramidal tract activity associated with a conditioned hand movement in the monkey," *J. Neurophysiol.*, 19:1011–1027 (1966).*

Fetz and Finocchio, "Operant conditioning of isolated activity in specific muscles and precentral cells," *Brain Res.*, 40:19–23 (1972).*

Frank, et al., "Present state of neural prostheses: visual, auditory, and motor," *Clin. Neurosurg.*, 24:337–346 (1977).*

Georgopoulos, et al., "On the relations between the direction of two–dimensional arm movements and cell discharge in primate motor cortex," *J. Neurosci.*, 2:1527–1537 (1982).*

Georgopoulos, et al., "The representation of movement direction in the motor cortex; single cell and population studies," In *Dynamic Aspects of Neocortical Function*, edited by Edelman, et al., New York: John Wiley & Sons, Chapter 16, pp. 501–524 (1984).*

Heetderks and Schmidt, "Chronic, multiple unit recording of neural activity with micromachined silicon microelectrodes," In *Proceedings of the RESNA '95 Annual Conference:* edited by A. Langton, RESNA Press: 659–663 (1995).*

Hetke, et al., "Silicon ribbon cables for chronically implantable microelectrode arrays," *IEEE Trans. Biomed. Eng.*, 41:314–321 (1994).*

Hornik and Stinchcombe, "Multilayer feedforward networks are universal approximators," *Neural Networks*, 2:359–366 (1989).*

Humphrey, "Representation of movements and muscles within the primate precentral motor cortex: historical and current perspectives," *Fed. Proc.*, 45:2687–2699 (1986).*

Humphrey (editor/contributor), *1979 Short Course Electrophysiological Techniques*, Society for Neuroscience, Atlanta, Georgia (Nov. 1–2, 1979).*

Humphrey, et al., "Patterns of activity across simultaneously observed cortical neurons during simple arm movements," *Federation Proceedings*, 29:791 (1970) Abstract.*

Humphrey, et al., "Predicting measures of motor performance from multiple cortical spike trains," *Science*, 170:758–762 (1970).*

Humphrey, "Relating motor cortex spike trains to measures of motor performance," *Brain Research*, 40:7–18 (1972).*

Humphrey, et al., "Some techniques for processing multichannel neuronal recordings," *Soc. Neurosci. Abstr.*, 18:848 (1992).*

Humphrey, et al., "Update on new techniques for processing multichannel neural/EMG recordings," *Soc. Neurosci. Abstr.*, 19:781 (1993).*

Humphrey, et al., "Intracortical recording of brain activity for control of limb prostheses," *Proc. Rehab. Eng. Soc. N. Amer.*, 15:650–658 (1995).*

Humphrey, et al., "Cortical control of neural prostetic devices," submitted to *Neural Prosthesis Program, National Institute of Neurological Diseases and Stroke, National Institutes of Health*, Final Report, submitted Sep. 1997.*

Humphrey, et al., "Cortical control of neural prosthetic devices," submitted to Neural Prosthesis Program, National Institute of Neurological Disorders and Stroke, National Insititues of Health, Quarterly Report #12, May 1, 1994–Jul. 31, 1994.*

Humphrey, et al., "Extracellular single–unit recording methods," *Neuromethods: Neurophysiological Techniques: Applications to Neural Systems*, 15:1–64 (1990) Edited by A. Boulton, et al., The Humana Press, Inc., Clifton, NJ.*

Humphrey, et al., "What features of voluntary motor control are encoded in the neuronal discharge of different cortical motor areas," In, *Motor Control: Concepts and Issues*, edited by Humphrey and Freund. New York: John Wiley & Sons, pp. 413–444 (1991).*

Kawashima, et al., "Fields in human motor areas involved in preparation for reaching, actual reaching, and visuomotor learning: a positron emission tomography study," *J. Neurosci.*, 14:3462–3474 (1994).*

Kennedy, "The cone electrode: a long–term electrode that records from neurites grown onto its recording surface," *J. Neurosci. Methods*, 29:181–193 (1989).*

Kwan, et al., "Spatial organization of primate precentral cortex in awake primates. II. Motor outputs," *J. Neurophysiol.*, 41:1120–1131 (1978).*

McBride, et al., "Axotomized corticospinal neurons cannot be retrogradely labeled with fluoro–gold one year after spinal cord transection," *Soc. Neurosci. Abstr.*, 16:984 (1990).*

Mauritz and Peckham, "Restoration of garsping functions in quadriplegic patients by Functional Electrical Stimulation (FES)," *Int. J. Rehabil. Res.*, 10 (Suppl 5):57–61 (1987).*

Najafi, et al., "Scaling limitations of silicon multichannel recording probes," *IEEE Trans. Biomed. Eng.*, BME–37:1–10 (1990).*

Najafi, et al., An implantable microelectrode array with on–chip signal processing, *IEEE J. Solid–state Circutis*, SC–21:1035–1044 (1986).*

Reed, et al., "Real–time, off–line control of a robot wrist from macaque MI recordings," *Soc. Neurosci. Abstr.*, 23:1556 (1997).*

Schmidt, et al., "Long–term chronic recording from cortical neurons," *Exp. Neurol.*, 52:496–506 (1976).*

Schmidt, et al., "Fine control of operantly conditioned firing patterns of cortical neurons," *Exp. Neurol.*, 61:349–369 (1978).*

Schwartz, A.B., "Motor cortical activity during drawing movements: population representation during sinusoid tracing," *J. Neurophysiol.*, 70:28–36 (1993).*

Soechting and Lacquaniti, "Invariant characteristics of a pointing movement in man," *J. Neurosci.*, 1:710–720 (1981).*

Stephan, et al., "Functional anatomy of the mental representation of upper extremity movements in healthy subjects," *J. Neurophysiol.*, 73:373–386 (1995).*

Stein, et al., "Bioelectric control of powered limbs for amputees," *Motor Control Mechanisms in Health and Disease*, 39:1093–1108 (Edited by J. E. Desmedt, Raven Press, New York) (1983).*

Vodovnik, et al., "Myo–electric control of paralyzed muscles," *IEEE Trans. Biomed. Eng.*, BME–12:169–172 (1965).*

Waters, et al., "Topographic organization of baboon primary motor cortex: face, hand, forelimb, and shoulder representation," *Somatosen. Mot. Res.*, 7:485–514 (1990).*

Wise, et al., "An integrated circuit approach to extracellular microelectrodes," *IEEE Trans. Biomed. Eng.* 17:238–247 (1970).*

Wolpaw, et al., "Development of an EEG–Based Brain–Computer Interface (BCI)," *Proc. Rehab. Eng. Soc. North America*, 15:645–648 (1995).*

Wyler and Burchiel, "Factors influencing accuracy of operant control of pyramidal tract neurons in monkey," *Brain Res.*, 152:418–421 (1978).*

Wyler, et al., "Operant control of precentral neurons in monkeys: evidence against open loop control," *Brain Res.*, 171:29–39 (Elsevier/North–Holland Biomedical Press) (1979).*

* cited by examiner

A

Log multiunit recording 
160

B

Rectified signal 
0.1 sec  50 uV
164

C

Integrator output 
166

D

S-H output 
168

E

Elbow position   lexed

Extended
161   162   163

STEP 1

STEP 2

ATTEMPTED MOVEMENT 116

|   | 1 | 2 | 3 | · · |
|---|---|---|---|---|
| N E U R A L  C H  1 | 0.8 | 0.2 | -0.7 | |
| 2 | -0.2 | 0.8 | 0.0 | |
| 3 | 0.7 | 0.4 | 0.5 | |
| 4 | 0.6 | -0.3 | 0.9 | |
| 5 | 0.0 | 0.7 | -0.1 | |
| 6 | 0.1 | 0.6 | 0.5 | |

| MOVEMENT | CHANNELS SELECTED 118 |
|---|---|
| 1 | 1,3,4 |
| 2 | 2,5,6 |
| 3 | 1,4 |

SYSTEM CALIBRATION METHOD

SYSTEMS, METHODS, AND DEVICES FOR CONTROLLING EXTERNAL DEVICES BY SIGNALS DERIVED DIRECTLY FROM THE NERVOUS SYSTEM

This invention relates generally to systems, methods and devices for interfacing between nerve cells (neurons) and external devices and, more particularly, to systems, methods and devices for extracting signals directly from the human brain and nervous system for use in the control of external devices.

BACKGROUND OF THE INVENTION

The human brain is an exceedingly complex processing system, which integrates continual streams of incoming sensory input data with stored memories, uses the input data and memories in complex decision processes at both conscious and unconscious levels, and on the basis of these processes generates observable behaviors by activation of its motor or movement control pathways and the muscles which these innervate.

In certain cases of traumatic injury or neurological disease, however, the brain is partially isolated from the periphery. Input data from certain senses are thus lost, at least for a portion of the body, as are many voluntary movements. Spinal cord injury is a well known example. With spinal cord injury, the pathways that link higher brain regions with the spinal cord and that are used for control of voluntary movements may be functionally transected at the site of injury. As a result, the patient is paralyzed, and (s)he can no longer voluntarily activate muscles that are innervated by regions of the spinal cord below the level of the injury. Despite the injury to their long fibers, however, many of the cells in these higher brain regions that control voluntary movement will survive and can still be activated voluntarily to generate electric signals for controlling voluntary movement. By recording directly from these cells with implantable devices (e.g., electrode arrays), signals generated by the cells may be "exteriorized" and used for the control of external prostheses, such as an assist robot or an artificial arm, or functional electrical stimulation paralyzed muscles.

Another example of such loss occurs in cases of amyotrophic lateral sclerosis (Lou Gebrig's Disease), in which the motor neurons which control muscles, as well as some of the brain cells that control these motor neurons, degenerate. In advanced stages of this disease, the patient may have completely intact senses and thought processes, but is "locked in", so that neither movements nor behavioral expressions of any kind can be made. Providing these patients with some way of communicating with the external world would greatly enhance their quality of life.

In sum, there is a need to develop a system for monitoring and processing the electrical signals from neurons within the central nervous system, so that the brain's electrical activity may be "exteriorized" and used for the voluntary control of external prostheses or assist devices. In this way, damaged pathways are circumvented and some control of the environment can be restored. Because the electrical fields of small groups of neurons drop off rapidly with distance from the cells, this system should include surgically implanted "tiny" electrodes or sensors, which can be placed in close proximity to the cells that generate command signals for voluntary movement.

Earlier attempts to utilize signals recorded directly from neurons for the express purpose of controlling external prostheses have, however, encountered a number of technical difficulties. A major problem is how to obtain stable electrical signals of sufficient amplitude for real-time control of an external device. Two previous approaches have been used, but neither is successful in this regard.

In the first approach, microelectrodes with small tips (<300 $\mu$m sq. surface area) have been used, which are positioned to within 10–100 $\mu$m of a single neuron, thus isolating its action potentials or "spikes" from that of other, more distant cells. In some cases, two or three adjacent neurons are recorded from simultaneously. In such cases, electronic devices are used to discriminate between the spikes of the individual cells and to sort their "spike trains" into distinctly recognizable signals. One problem with this approach, however, is that the effective "isolation" of the spikes of only one to a few neurons requires that the recording electrode be positioned in close proximity to the neurons. Thus, to obtain such records from a sufficient number of movement-related brain cells, scores of electrodes should be implanted in the hope that a few of them will be in just the right position to record signals from one or only a few movement controlling cells. Given the required proximity of the electrode and the cells, there is a high probability, however, that small movements of the former with respect to the latter will result in signal loss either because the electrode moves slightly away from the cells of interest, or closer to them, resulting in cellular injury. With blood pressure induced pulsations of the brain within the skull, such relative movement is not only possible but very likely.

In recent years, small, multichannel, micromachined (integrated circuit) electrodes have been developed for use in neural recording. Given sufficient recording channel density, these electrodes promised a partial solution to the electrode/tissue movement problem described above. If the signal was lost from one channel by electrode movement, there was hope that it might be "picked" up by an adjacent channel, which moved closer to the active neuron at the same time that the previous one moved away. However, problems have been encountered with these electrodes as well. For reasons that are not entirely clear, neural signals are lost from these electrodes over time, due apparently to the formation of polarization potentials at dissimilar metal junctions along the recording channel, or the ensheathment and thus biological insulation of the electrode by glial cells.

A second approach is to use electrodes with larger exposed recording surfaces (in the range of 0.5 to 1.5 mm sq. surface area). These low impedance electrodes have lower noise characteristics than those with smaller tips, and can reliably record the activity of hundreds to thousands of neurons at greater distances than can the latter. Indeed, low level electroencephalographic (EEG) or field potentials can even be recorded from the surface of the scalp. This approach thus can avoid the difficulty of different signal output levels caused by small movements between the electrodes and the selected cells encountered in the first approach. The use of the signals recorded in the second approach presents, however, a major problem for prosthesis control. In such recordings, the desired control signals may be of very low amplitude and may be "buried" within, or confounded by, EEG potentials from neurons that are not involved in voluntary motor processes. Thus, averaging must be used over many movement attempts to extract a usable signal. For this reason, this approach is less than desirable and perhaps not useful for real-time neural control of an external device.

Another problem, which occurs regardless of the electrode type used, is that neural signals may change over time for a variety of reasons: e.g., (a) naturally occurring cell death, which occurs randomly throughout the brain in adults; or (b) learning processes, which may, over time, alter the quantitative relationship between a neuron's activity and the external parts of the body to which it contributes voluntary control.

SUMMARY OF THE INVENTION

The present invention overcomes some of the difficulties described above with improved as well as new systems, methods and devices for obtaining signals directly from the brain or central nervous system, and for processing and utilizing these signals to control external devices. The systems described here are adaptable to a variety of signals from the brain or central nervous system as diverse as a) neurally generated electrical signals, recorded with microelectrode technologies from within the brain or with surface electrodes from extracranial sites; and/or (b) measures of localized blood flow that are correlated with neural activity, if techniques for miniaturization of current devices for making such measurements, in real time, are developed in the future. The external devices may include any device that can be controlled by processed electrical signals. These devices include, but are not limited to, artificial or prosthetic limbs; computer controlled, functional electrical stimulation of muscles of paralyzed individuals for the restoration of movement; robots or robotics components; computers or computer displays; or the teleoperation of robots and machines in hostile environments.

A preferred embodiment of the invention represents a unique blend of technologies from the fields of neuro- or electro-physiology, biomaterials science, neural signal processing, functional brain imaging (to guide implantation of sensors), and robotics or prosthetics. Included in the embodiment is a unique recording arrangement with bundles of six to ten small (20–50 $\mu$m in diameter), insulated, and flexible, noble metal wires that are arranged in a parallel or twisted array. The wire bundles are constructed so that each recording wire can collect multicellular signals from a small cluster of neurons, with tips that are incremental in length, so that many recording sites can be sampled along a single line of bundle insertion into the brain.

According to another preferred embodiment, software routines, together with corresponding hardware, are used to perform specific signal correlation, adaptation, and distribution as part of a general recalibration procedure. A unique signal processing method is provided to convert recorded neural signals into a resultant signal that is useful for control of an external device. And, for the first time, the disclosed system incorporates neural net software routines to map actual neural signals onto desired movement functions.

In accordance with a preferred embodiment of the invention, a robot arm is controlled by the neural signals recorded directly from the voluntary movement (motor) control areas of the cerebral cortex of a subject, such as an alert monkey. It can be appreciated, however, that the concepts and general procedures of using neural signals to control movements of a robot arm, as described in the various preferred embodiments of this invention, are valid for the control of any external device that can be manipulated directly or indirectly by electrical signals and are not limited to use with monkeys or other trained animals. The followings are the devices and stages of signal processing system implementation in a particular preferred embodiment of the invention.

(1) Sensors (e.g., Electrodes) and Sensor Arrays

Sensors and sensor arrays used in a preferred embodiment of the present invention should have appropriate geometry and size for the configuration of the neural implantation site, and the methods of construction of the wire bundles used in this embodiment allow such flexibility. In the present invention, these sensors are comprised of miniature, multichannel microelectrodes, either (a) fabricated with micromachining/photolithography methods, or (b) from noble metal (e.g., platinum or Pt) microwires, oriented along a single axis in a parallel or twisted array. For example, for extraction of signals from the "arm" control regions of the cerebral motor cortex of a human for the purpose of rudimentary control of a robot arm, an estimated minimum of 16–24 recording channels would be needed, with an electrode density of about 24/cm sq. Further, the implanted electrodes and arrays should be tailored to the required geometry of the implantation site, so that the electrode recording tips contact the correct cellular regions. The precise locations and shapes of the correct cellular regions can be determined prior to implantation by magnetic resonance imaging (MRI) and other brain imaging procedures. Multisite recording from cells with these regions is best accomplished by a wire bundle electrode array, with the recording tips of the bundled wires located at 0.5–0.6 mm intervals along the shaft of the array. When inserted normal to the cortical surface and aligned with cortical lamina V in the anterior bank of the central sulcus, this electrode array can sample activities from several clusters of the cortical output neurons that would normally control arm/hand movements. Because the wire bundle electrodes are made of a single noble metal, they do not suffer the loss of signals due to polarization potentials at dissimilar metal interfaces, as occurs in the micromachined electrodes constructed to date. Moreover, because the exposed (non-insulated) surface area of the wire electrode recording tip (400–1800 $\mu$m sq.) is larger than that typically used in an electrode designed for isolation of single neurons (150–300 $\mu$m sq.), signals can be recorded with the tips at a greater distance from the cells of interest, thus reducing the probability of cellular injury by relative movements of the electrode with respect to brain tissue.

(2) Electronic Microchips

According to one aspect of the preferred embodiment, electronic microchips are needed for various purposes, such as amplification, filtering, multiplexing, and radio transmission of signals to external receivers. In the examples given below, preamplification of multiple channels of neural data, multiplexing of neural data from multiple channels into a single data stream, and radio transmission out of the body of a subject would be accomplished by chips coupled to the electrode array, that are on the order of 2×2 cm sq. or less in size.

(3) External Receivers and Demultiplexers

According to another aspect of the preferred embodiment, external receivers and demultiplexers are needed for allowing the exteriorized data stream to be detected and reseparated into separate neural data channels, which can then be individually selected and mathematically transformed for control of specific devices (e.g. an arm prosthesis) or device components (e.g., separate parts of the arm prosthesis).

(4) Signal Usage, Correlation, and Adaptation Methods

Once the neural signals are exteriorized, the most appropriate use for each should be determined. For example, if signals are derived from the "arm" area of the motor cortex, some of the signals are related to shoulder movements, others to movements about the elbow, some others to movements about the wrist, and the rest to finger movements. (In the paralyzed individual, of course, the movements are "attempted" rather than actual voluntary movements.) If the signals are not derived from the motor cortex but are still under voluntary control by the subject, and are to be used for control of arm prosthesis movements, a determination should also be made as to which are the most useful signals for fine hand control, which for upper arm control, and so forth. Recorded neural signals may also change over time, due to electrode "drft" within the brain tissue (so that the electrode moves away from some cells and closer to others), natural death of cells (50,000–100,000 cells/day in the adult brain), or changes in the parameters of cell discharge in relation to movement which result from motor learning. Consequently, a procedure according to the invention adapts to, or partially compensates for, changes in recorded neural signals and their parameters over time, so that the same implanted electrode array is useful for control purposes for as long as possible.

A general neural prosthesis calibration procedure, including newly conceptualized signal correlation, adaptation, and distribution (software) routines, accomplishes all of these goals. In this procedure, the subject observes a set of simulated arm movements (or other activities) on a computer screen, and attempts to "track" or emulate these same movements with attempted movements of his/her own (paralyzed) arm. During the emulation process, the activity on each neural channel is cross-correlated with selected parameters of the simulated motion point rotation, position of the hand in space, speed of movement, etc.), to determine with which it is most highly correlated. The activity of this most correlated channel is then "routed" or "distributed" to the circuit which controls the device component or movement parameter with which it is most highly correlated. Since this calibration procedure can be performed readily by the subject or patient on a periodic basis, the optimal neural channels for control of the external device can be reselected and redistributed each time, thus providing a continuing adaptation to changing neural signals, regardless of the cause of these changes.

(5) Shaping of Signals for Optimal Device Control

Once a subset of signals has been selected for control of an arm prosthesis (or other device), according to one aspect of the preferred embodiment, the signals should still be mathematically combined for optimal control of that device. For example, if neural signals "x and y" out of some larger set of signals correlate well with attempted hand movements about the wrist, and they are to be used for that purpose in controlling an arm prosthesis, they should still be mathematically processed to optimize such control. By "optimal", it is meant that the processed signals should drive movements about the artificial wrist that match as closely as possible those model movements that are observed by the subject during the calibration procedure. To accomplish this, software networks are used for mapping actual neural signals onto desired movement functions; in the example referred to here, these would be the simulated arm/hand movements observed by the subject on the computer screen.

Accordingly, it is an object of the present invention to provide an improved system for recording neuronal signals directly from the brain or central nervous system for external device control.

It is another object of the present invention to develop an improved system which can be used with signals derived from small sets of selected single neurons, whose signals are separated from those of other nearby cells with electronic "spike" discrimination methods and are then recombined into a composite control signal.

It is a further object of the present invention to provide an improved system which can also be used with signals derived from small sets of neurons (2–10), whose signals are simply summed and electrically processed to obtain a useful signal for external device control.

It is yet another object of the present invention to provide multi-electrode sensors for recording from small clusters of neurons and providing signals that are midway between those obtained with the single neuron and EEG recording approaches described above.

It is yet a further object of the present invention to provide multichannel connectors and recording systems for use with the multi-electrode sensors.

It is also an object of the present invention to provide data reduction methods for converting the electrical activity signals recorded from clusters of neurons into useful intermediate control signals.

It is also another object of the present invention to provide an application of Neural Net algorithms for relating the intermediate control signals to movement parameters.

It is also a further object of the present invention to provide a novel calibration and adaptation method for periodically rematching recorded signals to the desired movements of an external device, so that compensation occurs for fluctuating signal amplitudes and/or motor learning.

BRIEF DESCRIPTION OF THE DRAWINGS

The accompanying drawings, which are incorporated in and form a part of the specification, illustrate preferred embodiments of the present invention and, together with description, serve to explain the principles of the invention. In the drawings.

DETAILED DESCRIPTION OF THE DRAWINGS

Reference will now be made in detail to preferred embodiments of the invention, non-limiting examples of which are illustrated in the accompanying drawings.

A. Overview

Figure 1:
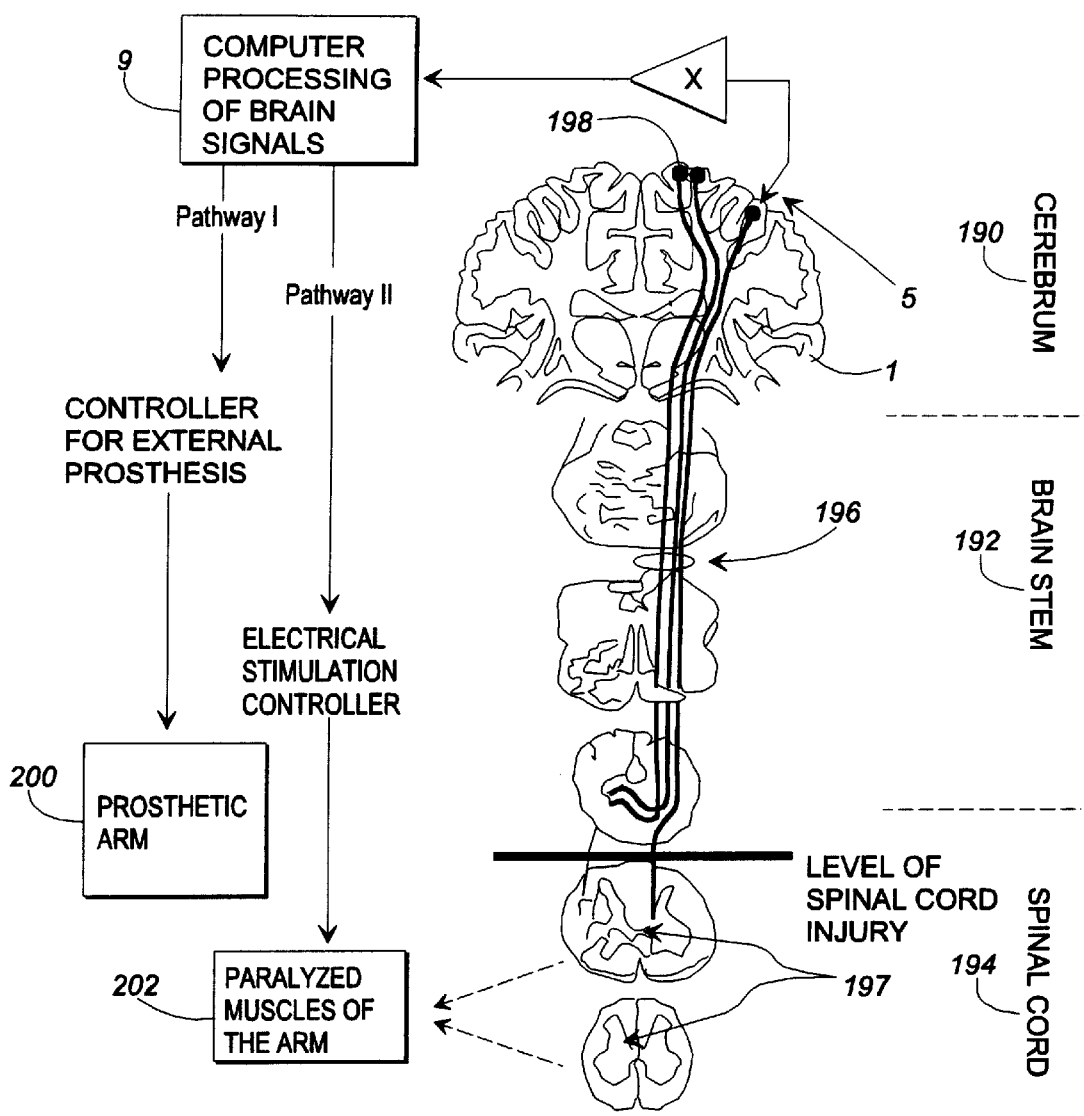
FIG. 1 is an exemplary diagram of a system according to the present invention for use by a subject with a spinal cord injury in voluntary controlling an external device.

With reference to FIG. 1, a system according to a preferred embodiment of the invention uses signals from cells in higher brain regions 1 can be activated voluntarily by a patient/subject, to in turn control external devices such as an artificial arm 200 and electrical stimulation of paralyzed muscles of an injured arm 202. FIG. 1 shows sections through various levels of the cerebrum 190, brain stem 192, and spinal cord 194. Also shown are pathways 196 that link the motor (movement control) areas of the cerebral cortex 198 with the spinal cord motor neurons 197 that control muscles of the arm 202. By recording directly from the cells in higher brain regions 1 with implantable devices 5 (e.g., electrode arrays), signals collected at the cells can, after processing by computer and electronic interfaces 9, be "exteriorized" and used for the control of external prostheses, such as the artificial arm 200 (external pathway I) or the electrical stimulation of paralyzed muscles 202 (pathway II).

Alert monkeys that are trained to make specific arm movements in order to receive small food or juice rewards are used as subjects. Under surgical anesthesia and sterile conditions, arrays 5 of microelectrode sensors are implanted into the motor (voluntary movement control) areas of the animal's cerebral cortex 198, opposite the trained arm, preferably according to one of the methods as demonstrated in FIGS. 5–6. When the animal is fully recovered, signals from sets of neurons whose electrical activity is correlated in time with performance of these arm movements are identified, and the signals are processed mathematically for control of the robot arm as shown in FIGS. 7–11. This processing is such that the neural signals that are selected for control of a particular part of the arm (e.g., movements about the elbow) will, when applied to the controller for that part, produce robot arm movements that are very similar to those made by the animal. These "off-line" simulations allow of adjusting neural net parameters for optimal control of the robot arm as shown in FIG. 12. Again using positive reward procedures, the animals are then trained in 1 hour long daily sessions to adapt to the movements of the nearby robot arm, which their brain signals now begin to move roughly in parallel with their own arm movements. Delivery of the food rewards is then gradually made contingent not upon the accuracy of the animal's own arm movements, but upon those of the robot arm. Eventually, the animal's own movements can be temporarily restrained (by securing the sleeve of its training jacket), and he/she can obtain food solely through directly controlled movements of the robot arm with the neural signals recorded directly from his/her brain. The systems, methods, and devices according to various embodiments of the current invention can also be used by medical use with humans.

B. Sensors/Electrodes for Recording Neural Signals

Figure 2:
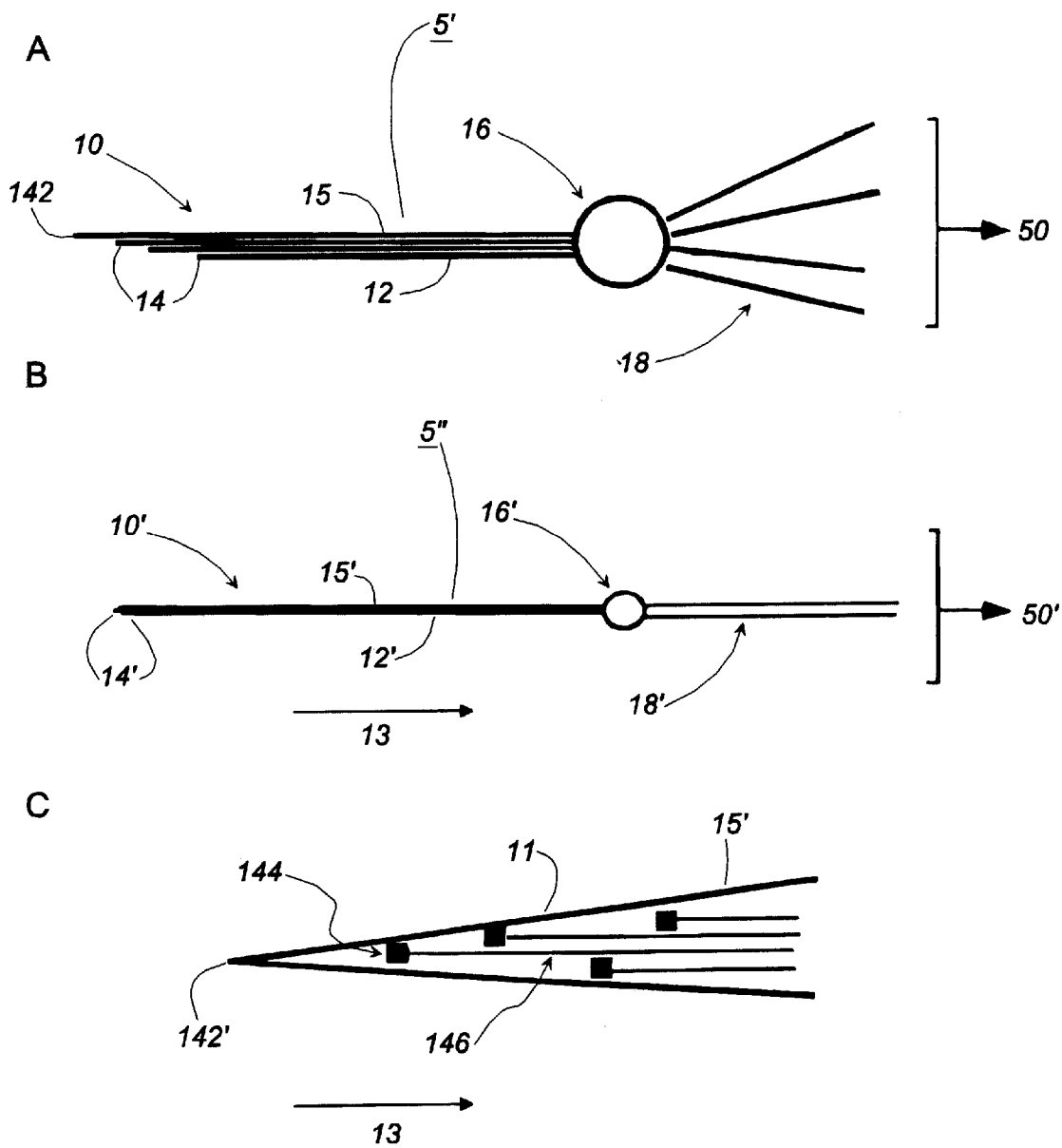
FIGS. 2(A) to (C) are schematics of sensors (electrodes) and sensor arrays according to the present invention for recording brain activity.

Examples of the implantable devices 5 are shown in FIGS. 2(A) to (C). FIG. 2(A) shows a preferred embodiment of sensors or a sensor array 5' according to the present invention for recording from cortical cells of a brain for extended periods of time. Six to ten small (25 to 50 $\mu$m diameter), insulated, noble metal, preferably Pt or Gold, wires 12 are bundled in a parallel or twisted array 10, with staggered length so that the exposed recording tips 14 end at different cortical depths (from the surface of the brain) when inserted into the brain.

In one embodiment of the invention, the wires 12 are constructed of 25 $\mu$m diameter Pt, insulated by a thin layer of Formvar, Isonel, or some other suitable material 15 obtained from the California Fine Wire Co. of Grover Beach, California. A completed wire bundle 10 made with 25 $\mu$m wire is approximately 75 $\mu$m in diameter. In another embodiment of the invention, the wires 12 are constructed of 50 $\mu$m diameter wire. A completed bundle 10 made with 50 $\mu$m diameter wire is about 150 $\mu$m in diameter, and is 15–35 mm long from electrode tip 14 to a connector assembly 50. Electrodes made with the 50 $\mu$m diameter wire isolate the electrical activities of small clusters of 3 or more neurons as well as those obtained with the 25 $\mu$m diameter wire.

The wires 12 are held in position with respect to one another by a light-cured optical cement bead 16, placed 6–8 mm from a most distant wire tip 142. The recording tips 14 of the individual wires 12 are located from 2 to 6–8 mm distal to the bead 16. The difference in length from one tip to its neighbor tip is substantially equal in one embodiment of the invention, about 0.5 to 0.6 mm, but these distances can be varied, depending upon the implantation site and its geometry. The bead 16, in one embodiment of the invention, is a small (0.5–0.6 mm diameter) drop of UV-curable acrylate, cured with 30 sec of UV exposure from a small, focused, UV gun. The cement bead 16 is also used for handling and manipulating the array 5' during its insertion into the brain, because of the bead's degree of rigidity. On the proximal side of the bead 16, the wires 18 separate to bundle loosely to the implanted connector assembly 50 (see below). By inserting several staggered arrays 5' along the central sulcus of the cerebral cortex 198, where major motor areas exist, it is possible to place them all within the cortical layer that contains the corticospinal neurons that participate normally in the control of voluntary movement. MRI is used prior to surgery to locate this region precisely in relation to anatomical landmarks on the skull, thus guiding electrode implantation. Placement of eight to twenty of sensor arrays 5' in wire bundle form ensures recording from sufficient numbers of cells to capture a useful number of control signals.

An alternative type of sensor array 5" is shown in FIGS. 2(B) and 2(C), where the latter is an enlarged view of recording tips 14' shown in FIG. 2(B). In principle, the sensor array 5" is similar to the bundled wire array 5' shown in FIG. 2(A), except that in this case the entire array 5" is constructed by micromachining or photolithographic techniques. In the embodiment shown, each recording channel or "wire" 12' is a very thin (4–10 $\mu$m wide) strip of metal, left on a silicon substrate after etching away the surrounding metal. A long, sharp, insulating silicone substrate 11 contains six to eight separate recording channels 146, which end in uninsulated recording pads 144 at various sites along a sensor shank 13 which, when covered with a bead 16' of epoxy or similar material, can be used for gripping and manipulation (with fine tools) of the sensor array 5". Again, an enlarged bead 16' or disc region occurs along the shank 13. On the opposite side of this bead 16', separate (insulated) wire channels 18' course to a 1.0 mm diameter pad 50'. Though more desirable because of their small size and precise geometry, long-term recording was less successful with the micromachined sensor array 5" than with the sensor array 5' in wire bundles 10 described above and shown in FIG. 2(A). Reasons for this include micromachined sensors greater fragility, difficulty in making connections with their channels, polarization potentials between their dissimilar metals which block electrode conductance, the encasement of the electrodes by glial cells, and insulating them from neural signals, when they are implanted.

Figure 3:
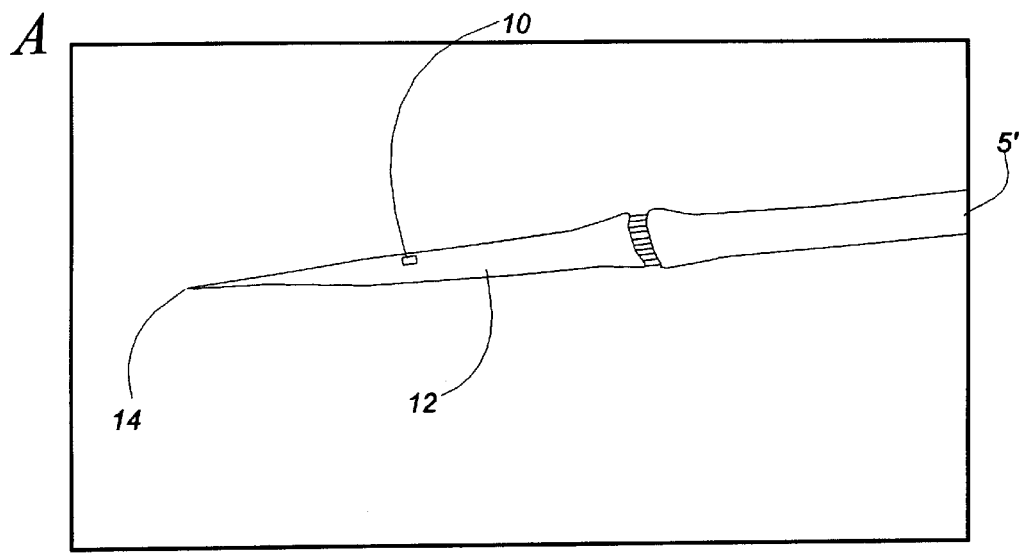
FIGS. 3(A) and (B) are photomicrographs of recording arrays of the present invention used to monitor the activity of sets of cortical neurons.
Figure 3:
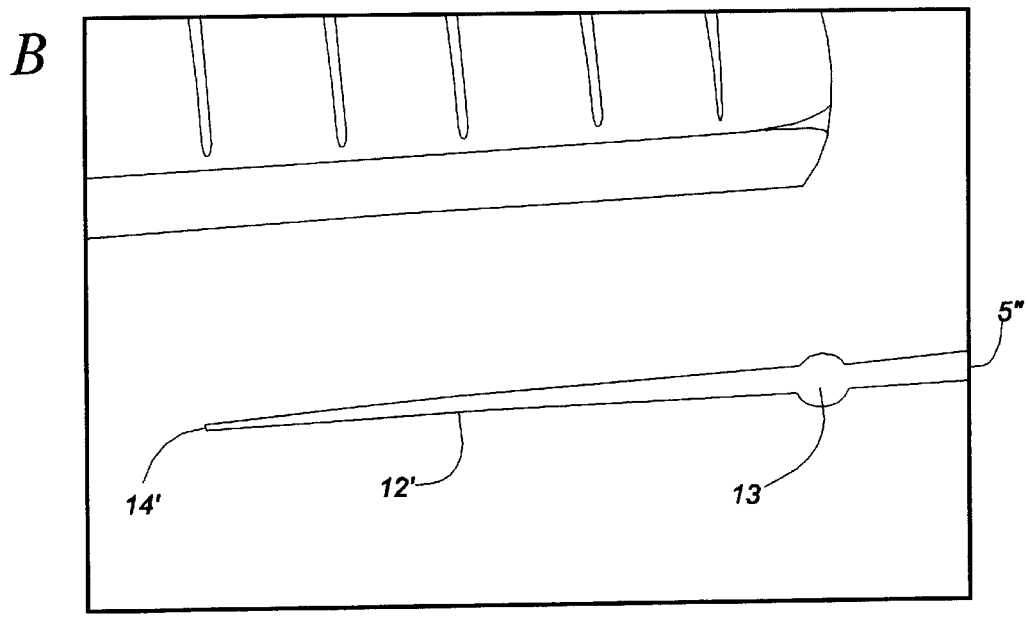

Photomicrographs of the arrays 5' and 5" are shown in FIGS. 3(A) and (B), respectively. FIG. 3(A) discloses a bundle 10 of pure platinum wires 12, insulated except at the tips 14. FIG. 3(B) shows a photo-lithographically prepared (micromachined) array 5". Thin, insulated conductors 12' travel from non-insulated recording pads 14' (Oust visible along the shank 13 of the electrode 5"), up a longer cable, and to a dispersed pad where electrical connections can be made.

Figure 4:
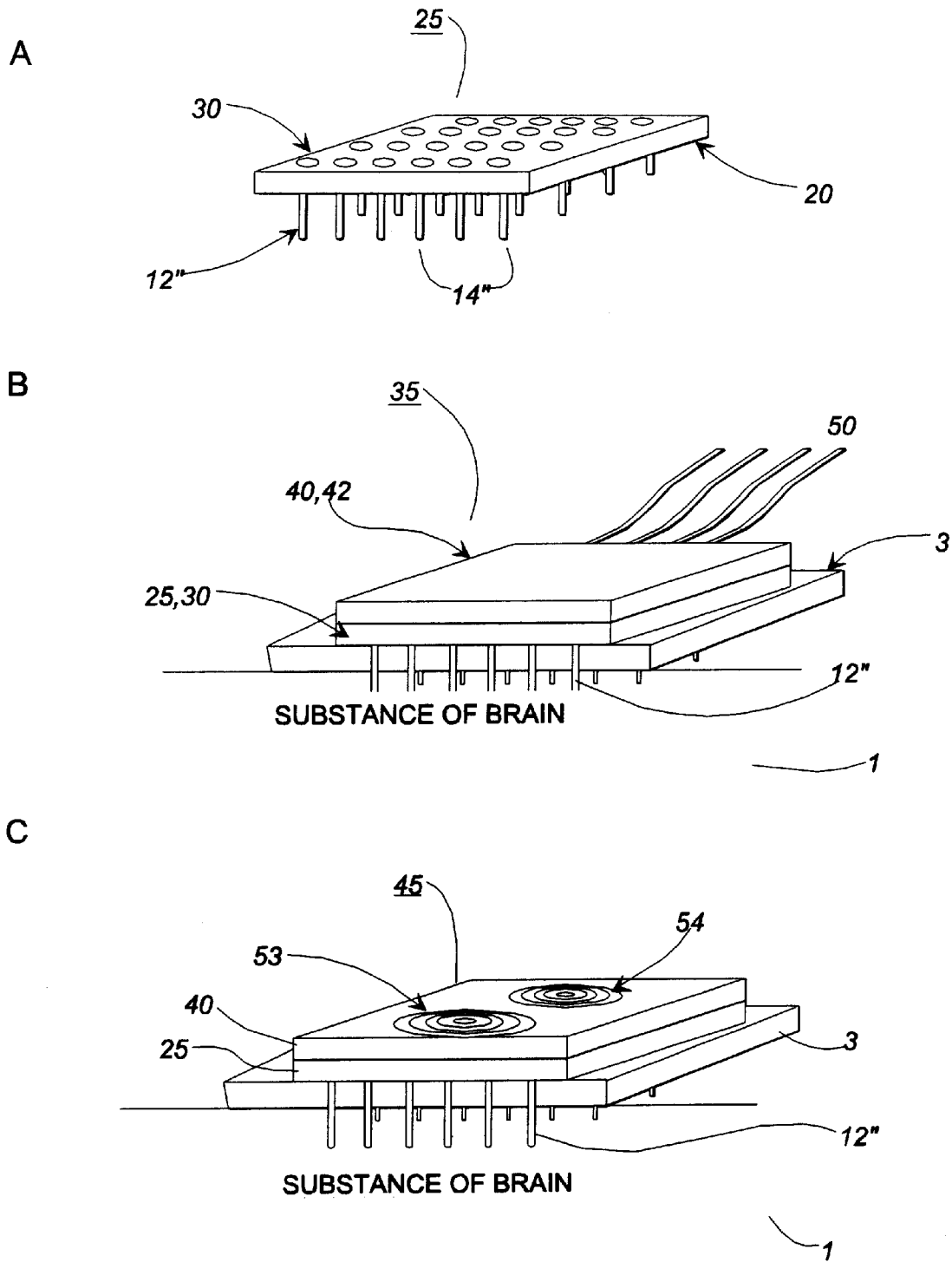
FIGS. 4(A) to (C) are diagrams of other embodiments of electrode arrays and methods for bringing power to and taking neural signals from an implantable microchip.

FIGS. 4(A) to (C) show yet other types of electrode arrays that may be used in the present invention. In FIG. 4(A), "n" parallel electrodes 12", each 2.5–3.0 mm in length, protrude from a silicone wafer 20 as an insulating substrate, each in electrical continuity with a gold contact pad 30 on the opposite surface of the wafer 20. The electrodes 12" are insulated except at the tips 14'. Each of the electrodes 12" can be made from a short length of 90% Pt and 10% iridium wire or other noble alloy, which has sufficient stiffness over its short length to allow penetration of the pial covering of the brain and insertion into the cerebral cortex. An electrode array 25 of this type with each electrode 12" being a platinum plated silicon probe, but not in bundle form, is commercially available. As shown in FIGS. 4(B) and 4(C), an electrode array 25, as shown in FIG. 4(A), can be bonded to a second microchip 40 that contains "n" pads that mate precisely with those on the electrode array 25. The microchip 40 and the electrode array 25 are bonded in close contact and are then hermetically sealed. The microchip 40 may contain integrated circuits 42 that provide for amplification of the signals in each of the n electrodes or channels, and for multiplexing these signals into a serial data stream for transmission out of the brain 1. The microchip 40 and electrode array 25 set upon the meninges 3 (tissue coverings of the brain 1), but beneath the skull (not shown), and the electrodes 12" penetrate the meninges 3 into the substance of the brain 1 so that neural signals can be directly collected therefrom. The electrodes 12" which protrude from the array 25 may be individual wire leads, or short bundles of the type described above.

Figure 5:
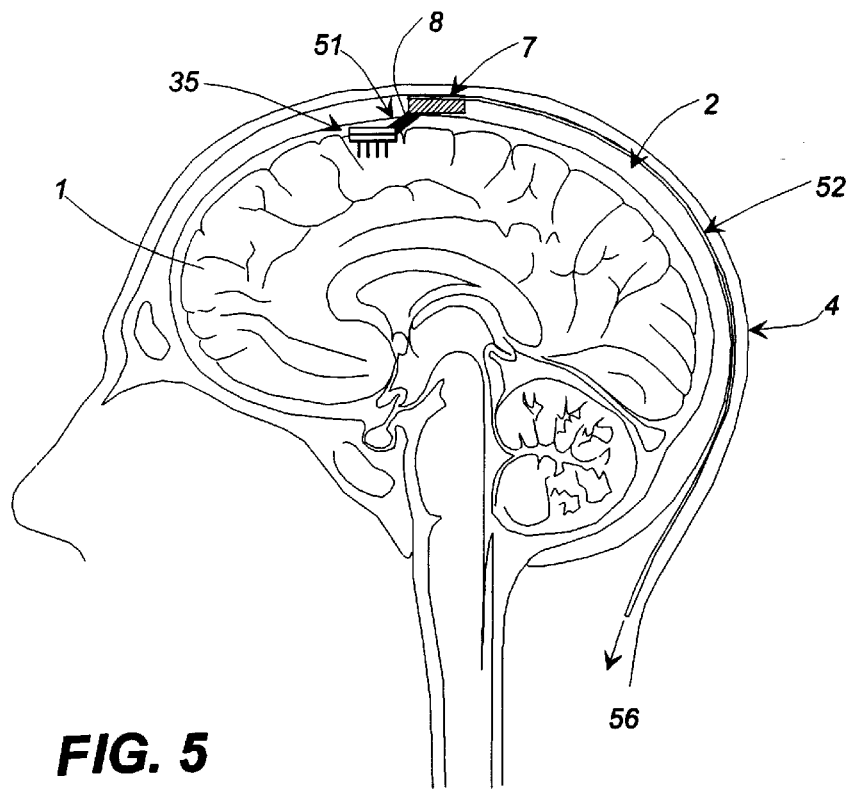
FIG. 5 is a diagram of an implanted device for externalizing neural signals for control of prosthetic devices.
Figure 6:
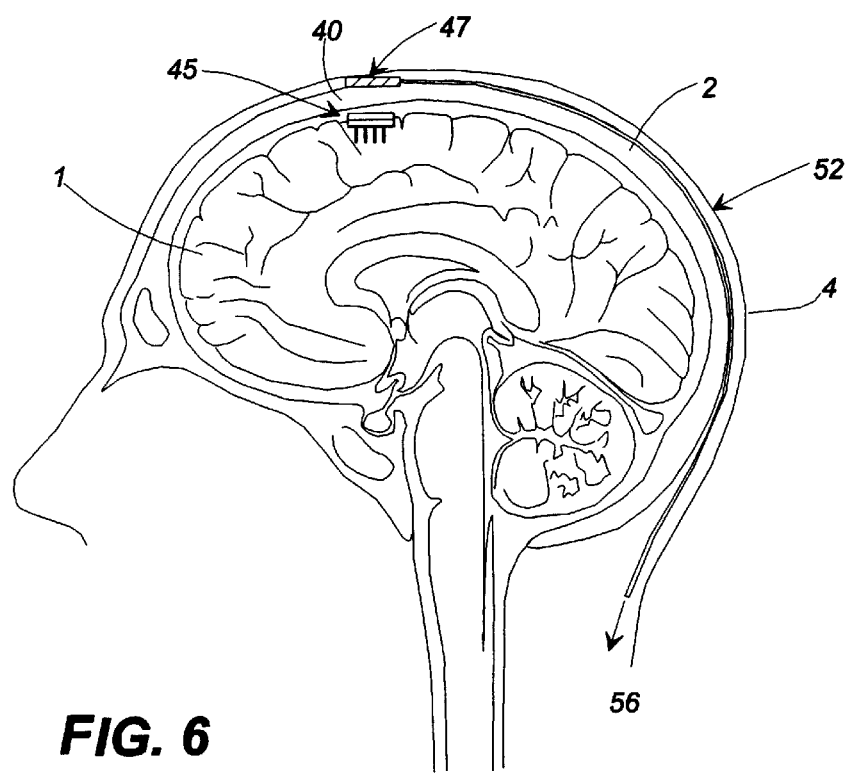
FIG. 6 is a diagram of an implanted device according to a second embodiment for exteriorizing neural signals.
Figure 7:
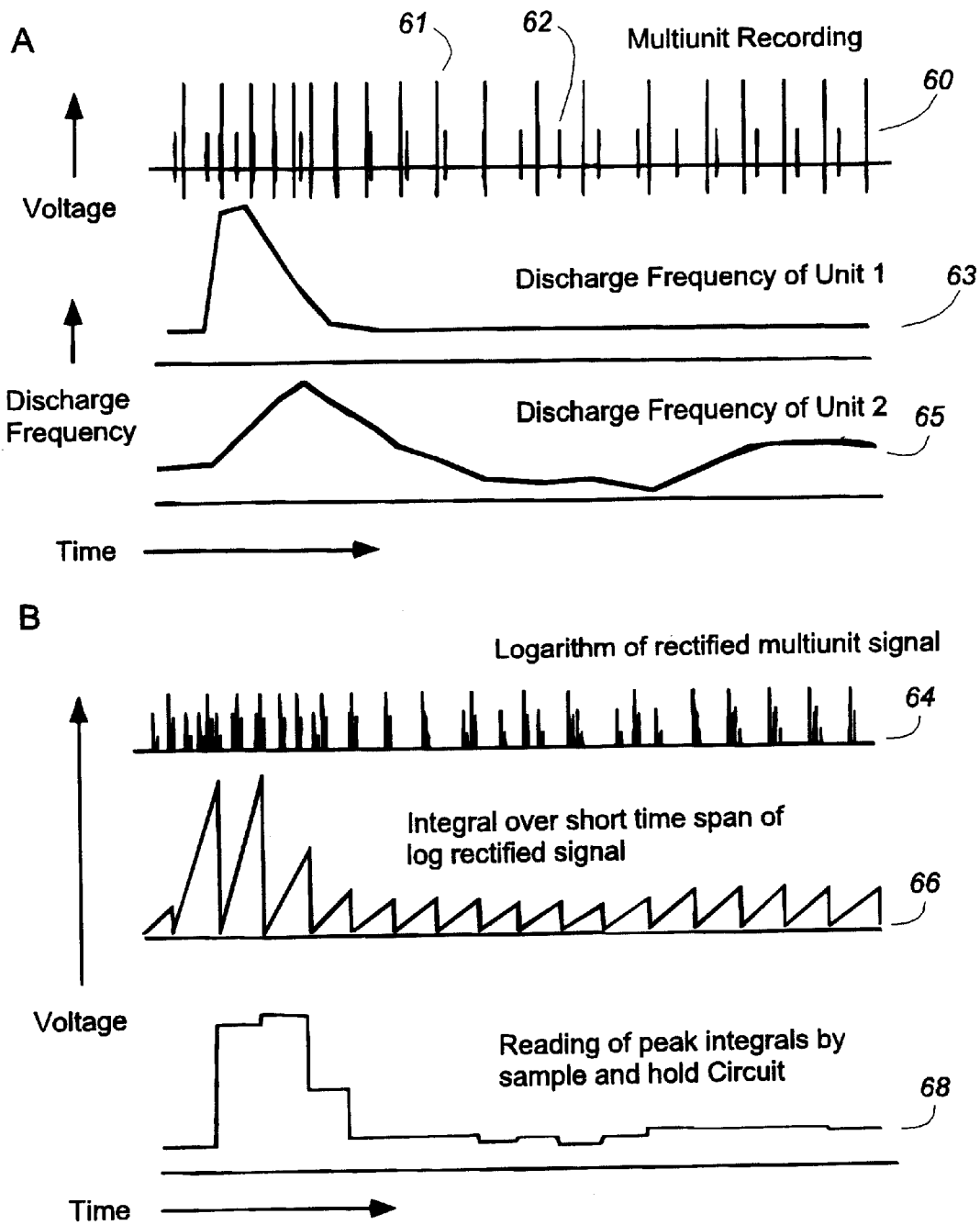
FIGS. 7(A) and (B) are waveforms schematics of signals in the second stage of processing of recorded multiunit neural signals.

FIGS. 5 and 6 illustrate two possible ways that the signals may be led from the brain 1 to external processing units. The first is a communication channel established by a hardware connection as shown in FIG. 5, and the other is a communication channel established by a wireless mechanism as shown in FIG. 6.

Referring first to FIG. 5, in connection with FIG. 4(B), the implanted electrode array 35 has the first stage electronics circuitry 42 for signal processing (multichannel amplification and multiplexing) attached. Signals from the circuitry 42 are sent via a small, flexible cable 51 to a second stage device 7 implanted within the skull 2. An implant/skull junction 8 is hermetically sealed. This device 7 relays power from an implantable battery pack 56 connected to it by leads 52 beneath the skin and scalp 4. The implanted electronics 51, 7 and 42 are preferably programmable and contain circuitry for selecting (gating on) the neural channels to be used and for setting other recording parameters. They also preferably contain a transmitter for relaying the neural signals by RF signal to a receiver, which in turn relays it to demultiplexing and the later stages of neural signal processing described in more detail in the subsequent text and figures.

Referring now to FIG. 6, in connection with FIG. 4(C), there is shown an alternative implant method, according to a preferred embodiment of the invention, which uses a wireless mechanism, thereby allowing the cranium (skull) 2 to be reclosed, and thus reducing chances of infection. The electrode implant array 45 contains the microchip 40 which has multichannel amplifiers, multiplexing circuitry, and an RF transmitter. Attached to the microchip 40 are two coils 53 and 54 (as shown in FIG. 4(C)). One coil 53 allows power to be transmitted to the implant array 45 via a coil in an external unit 47 by induction, and the second coil 54 allows transmission of the multiplexed, multichannel neural signal out as a serial data stream. The external unit 47 contains a power coil, and a chip for conversion of DC voltages into the AC voltages that are necessary for inductive coupling to the internal coil 53. All devices are implanted beneath the skin. Battery packs 56 and the external unit 47 can be changed by simple surgical procedures if necessary. With the technique shown in FIG. 6, the skull 2 is closed completely. While coils are used to describe the way that signals are led from the brain to external processing units by a nonresonant wireless mechanism, other kinds of devices, such as LC circuits or low pass filters, can be utilized to establish a resonant wireless mechanism to relay the signals as well.

Both techniques shown in FIGS. 5 and 6 allow for complete implantation of the first stages of the system. In the first method (FIGS. 5 and 4(B)), a junction 8 is hermetically sealed between the cranial implant site 51 and the second stage device 7. In the second method (FIGS. 6 and 4(C)), the skull 2 is resealed completely. In both cases, surgical removal and updating or replacement of implant components is possible if necessary.

When these electrode arrays and devices are to be implanted in humans, functional MRI (fMRI) technology may first be used to identify those brain regions that the patient still has under voluntary control, thus allowing precise, functional placement of the implants and the recording electrodes.

C. Second Stage Processing of Neural Signals

The types of neural signals recorded with the electrode technologies described above are shown schematically in FIGS. 7(A) and (B). Typically, the recorded neural signals include action potentials or "spikes" (brief, voltage transients) which signal the discharge of small groups of cells located near the electrode recording tips 14. Because these cells are of different sizes and distances from the electrodes 12, 12', or 12", their action potentials will vary in shape and amplitude, and may be separated electronically or with computer software on the basis of these differences. FIG. 7(A) shows, for example, a hypothetical voltage recorded overtime at one tip 14 of the multiwire bundle 10. The record shown in FIG. 9 can be seen to be composed of spikes of different amplitudes. At this stage, one of two major types of second stage processing of the recorded signals can be used.

The first type of processing is spike discrimination method known to persons skilled in the art. Still referring to FIG. 7(A), an example is shown in an upper trace 60 where two distinct trains 61 and 62 of action potentials, from two different neurons or single "units" as they are often called by persons skilled in the field, are interleaved in the single electrode recording. The single unit spike trains 61 and 62 can be separated electronically on the basis of differences in their spike waveforms or amplitudes, and the discharge frequency of each neuron (frequency=1/interval between spikes or action potentials). This separation yields two or more useful control signals, as shown in the lower traces 63 and 65 of FIG. 7(A), from a single electrode. Such spike train separation is, however, expensive in terms of needed hardware and software, thus raising the cost, bulk and complexity of any surgically implanted device. Moreover, single neurons may be damaged by small movements of the electrodes 12, 12', or 12'', and their signals may be lost. Since the brain 1 can move slightly within the skull 2, particularly in relation to respiratory or cardiovascular induced changes in intracranial pressure, such relative movements can easily occur. Thus, while the spike discrimination method is one in current use today by many neurophysiological investigators, there have been as yet no published solutions to the problems of mechanical recording stability.

To circumvent the problems of mechanical recording stability, a new type of second-stage processing of recorded neural signals has been developed as demonstrated in FIG. 7(B). In this new method, the exposed surfaces of the recording electrode tips 14 are made slightly larger (400–1800 $\mu$m sq.) than is optimal for the isolation of single cell discharge, so that the spikes of several neurons are picked up simultaneously at each electrode tip 14. Furthermore, to reduce the possibility that the larger spikes of very nearby cells will dominate the record, only to be later lost through damage to the cells by the electrode 12, 12', or 12'', the voltage signal is converted logarithmically. This conversion de-emphasizes the voltage contribution to the multi-unit record from nearby cells, and emphasizes that from the more numerous, more distant cells. The signal is then electrically rectified, yielding a signal 64 like that shown in the top trace of panel B. This trace 64 is actually the log rectified representation of the trace 60 in panel A. Thus, the resulting signal S(t) 64 is given by: $S(t)=\log|V(t)|$, where $|V(t)|$ is the absolute value of the recorded multiunit voltage signal 60. Note that S(t) 64 is a positive function of both the log amplitude and the frequency of occurrence of the neural spikes. It is thus a measure of the density of neural activity in the vicinity of the electrode tip 14, a signal that tends to be more stable over time than the single unit method of recording described in the first method of processing neural signals.

Next, to convert this signal 64 to one that is more useful for control of some external device, S(t) 64 is integrated over a short time period to yield a signal 66 whose peak values correspond to the integral of activity over the preceding time interval (see FIG. 7(B)). A 33 msec integration interval is chosen because it is synchronized with the video recording frame duration, and it is found to be useful for experimental purposes. In practice, it should be a period of no longer than ($\frac{1}{2}$f), where f is the highest frequency component of the device movement speed that one wishes to generate. For human natural movement, f is on the order of 5 Hz. Thus, the integration period should not exceed ($\frac{1}{10}$)=0.1 sec=100 msec. At the end of each integration interval (33–100 msec), the peak value 67 of the integral 66 is then "read" by an electronic sample and hold (S-H) circuit, which is known to persons skilled in the art, the integrator is reset to zero, and another period of integration begins. The S-H circuit holds its value until the end of the next interval, and then jumps instantaneously to the new reading. Smoothing of the S-H output provides an analog signal 68 that is "smoother" than the original neural signal 60 yet still proportional to S(t) 64. Moreover, the analog signal 68 is much more useful for external device control because unwanted signals outside the frequency range of interest have been eliminated.

Figure 8:
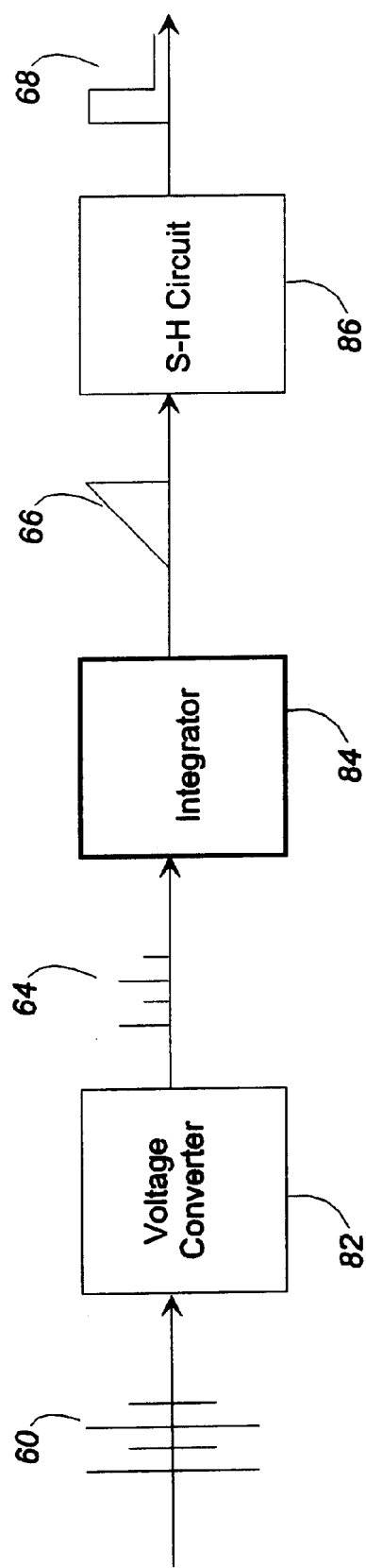
FIGS. 8 is a block diagram of a second stage of processing.
Figure 9:
FIGS. 9(A) to (E) are waveforms schematics of signals arising in the processing of multiunit recordings from the arm area of the sensorimotor cortex of a monkey.
Figure 9:
Figure 9:
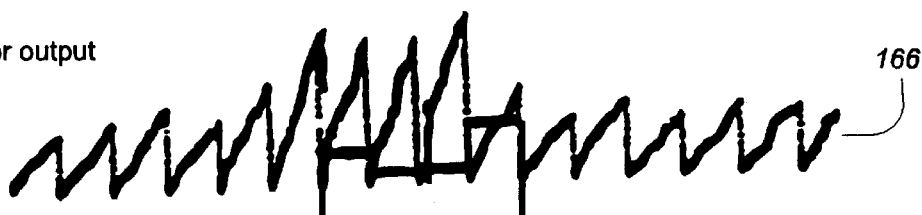
Figure 9:
Figure 9:
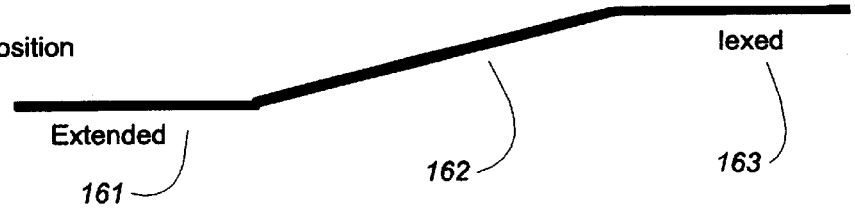

An example of the second stage of signal processing is shown in FIG. 8. During this stage of the processing, the recorded neural signals 60 having spikes are first converted logarithmically and rectified by the voltage converter 82 to yield a signal 64. Then, the signal 64 is integrated by an integrator 84 over a time period of no longer than ($\frac{1}{2}$f) to produce an integral 66, where the integrator 84 is connected to the voltage converter 82 as well as a S-H circuit 86. The S-H circuit 86 receives the integral 66, reads the peak value of the integral 66, and provides an analog signal 68 after smoothing.

As an illustration, an example of these operations performed upon actual neural recordings from the brain of an alert monkey is shown in FIGS. 9(A) to (E). The trace in FIG. 9(A) shows the log amplitude of the multi-unit activity 160 recorded from a cluster of neurons in the sensorimotor cortex of the monkey, during flexion (161–163) of his elbow as shown in FIG. 9(E); note the increased activity during elbow flexion 162. The trace 164 in FIG. 9(B) shows the absolute or rectified value of the signal 160. The trace 166 as shown in FIG. 9(C) shows the output of the short interval, resettable integrator, and the trace 168 as shown in FIG. 9(D) shows the output of the S-H circuit that "reads" the value of the integrator at the end of each short integration period. The recordings are from experiments with a trained monkey, carried out during development of the technologies disclosed here. The time/voltage calibrations are 0.1 sec and 50 microvolts.

D. Third and Later Stages of Signal Processing

Figure 10:
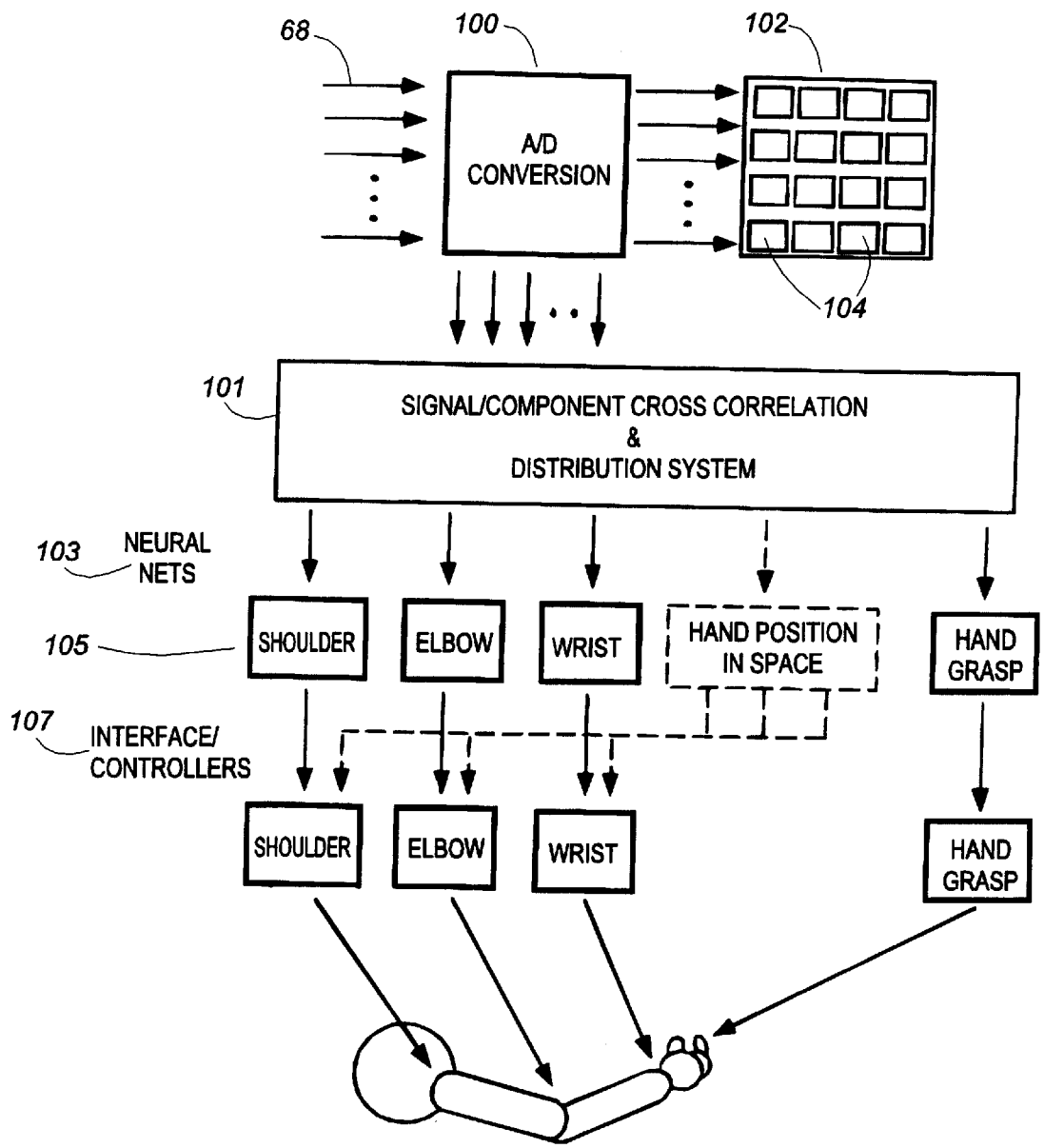
FIG. 10 is a schematic of third and later stages of neural signal processing system, and an example of operation of the neural prosthesis for control of a prosthetic or a robot arm.

A summary of the third and subsequent stages of signal processing is shown in FIG. 10 according to a preferred embodiment of the present invention. The processed signals 68 from the S-H circuit 86 are digitized by an analog/digital (A/D) signal converter 100 and then fed in parallel to (a) a multichannel display system 102, and (2) a signal/movement cross correlation and distribution system 101. The display system 102 is an n-cell matrix, where "n" is an integer and each cell 104 in the matrix 102 represents a separate neural data channel. The system 102 provides a quick overview of the pattern of activity across the "n" selected neural recording channels for each of the integration periods described above, and is extremely useful for initially "focusing in" on those channels that are most active during particular actual or attempted movement. The display system 102 includes a LED display, where the intensity of the LED lighting is a positive function of the level of neural activity in that channel, or a small computer screen which displays the ongoing level of activity in each channel in the form of color-coded values. Typically, the range of neural activity is divided into eight levels for monitoring purposes, though it is actually digitized for subsequent processing with 12-bit accuracy.

Figure 11:
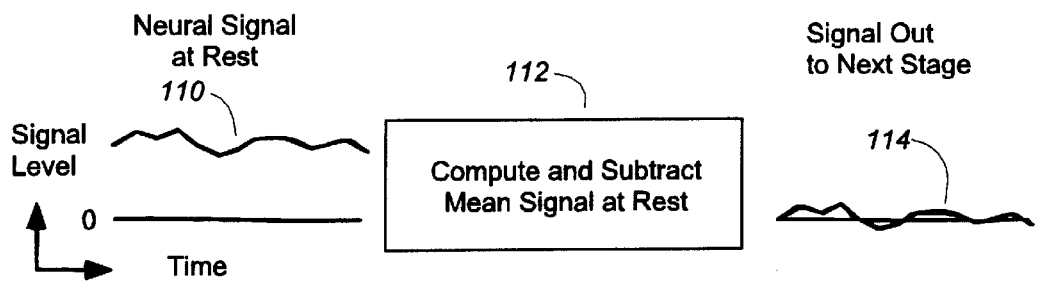
FIG. 11 is a diagram of operations performed by a movement calibration and signal distribution system depicted schematically in FIG. 10.
Figure 12:
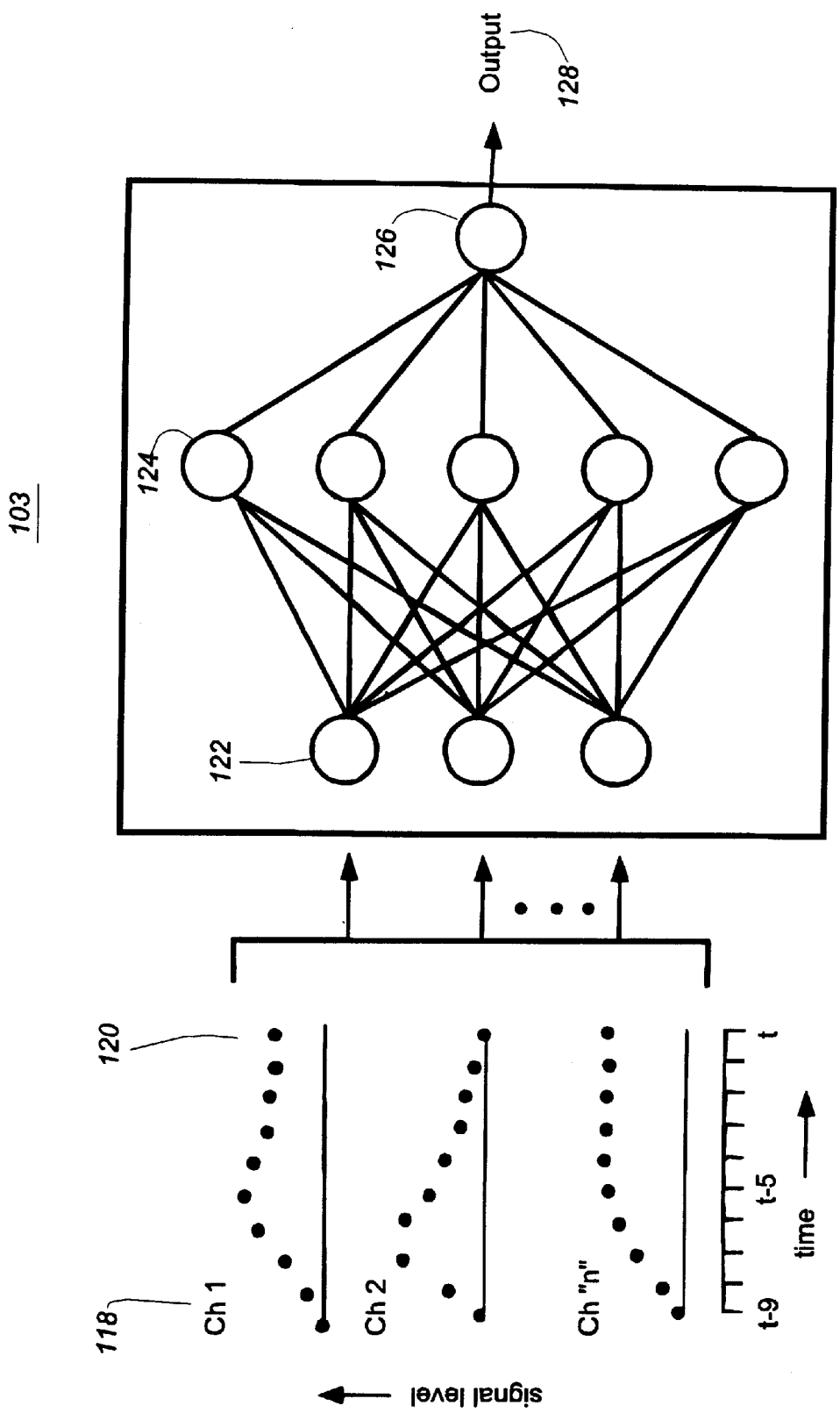
FIG. 12 is a schematic of an artificial neural net used to process neural input data before passing it to a peripheral device controller.

The signal/movement cross correlation and distribution system 101 is preferably a "C" language software routine which performs the following operations as illustrated in FIG. 11 according to a preferred embodiment of the present invention:

(1) Determination of mean signal levels 112 on each channel when the subject is at "rest";

(2) Subtraction of the mean resting signal level 112 for each channel from the ongoing signal 110 of that channel, thus yielding a time-dependent signal D(t) 114 that departs from zero only when a movement is attempted;

(3) Computation of the cross correlations between D(t) 114 and the computerized display 116 of model arm (or joint) position, velocity, or acceleration (see the correlation table in step 2, FIG. 11) as observed by the subject during the calibration procedure described in detail below;

(4) On the basis of these correlations, selection of the channels 118 that will be most useful for control of movements or movement-related parameters of the external device;

(5) Routing/distribution of the selected channels 118 to the artificial neural nets (shown in FIG. 12) that will "shape" that signal for control of particular movements or of any other external device parameter.

Refer now back to FIG. 10. After selection of the subset 118 of channels that will be used to control a particular part of the external device, in this example movements about one of the "joints" in a robot arm, the signals on the channels 118 are fed to a three-layer, software or Artificial Neural Net (ANN) 103 for further processing, before passing to a peripheral device controller 107. After a succession of attempted or actual movements 105, in which each ANN 103 learns to "map" selected neural data channels 118 onto some measured output parameter, the ANNs 103 will thereafter shape the input signals appropriately for device control. In the case of the paralyzed individual, the output parameter would be a desired or "calibrated" movement of the arm, or movement about a major joint in the arm, that (s)he observes on a computer display and "tries" to emulate with his/her own paralyzed arm. This "calibration" procedure is described in more detail in the next section.

The properties of a current ANN 103 used for this purpose are depicted in FIG. 12. The preprocessed neural signals 120, with resting back-ground levels removed, are fed from the particular neural channels 118 selected for control of wrist movements of a robot arm to each input node of a software ANN 103. The ANN 103 has a standard three layer, feedforward network that is trained using back propagation with momentum. The first layer contains three input nodes 122, the second, hidden layer contains five nodes 124, and the output layer has a single node 126 (scalar output). All of the nodes are fully interconnected in a strictly feedforward manner; i.e., each node in a layer is fully interconnected in a feedforward manner to every node in the next layer, and only to those in the next layer. For instance, each input node 122 receives input data 120 from all of the selected channels 118, it then sends an output to each node 124 in the middle or hidden layer. Each node 124 in the hidden layer receives inputs from each of the nodes 122 in the input layer. In turn, all nodes 124 in the hidden layer send outputs to the single node 126 in the final or ANN output layer. To further smooth out data transients that are outside of the control frequencies of interest (0–5 Hz), each data point fed to the ANN 103 comprises a running average of the current value of the neural signal in channel "m" (at time "t") plus the previous nine values of that signal (from time t-1 to t-9). This averaging period was determined by trial and error and may be changed to other values.

Figure 13:
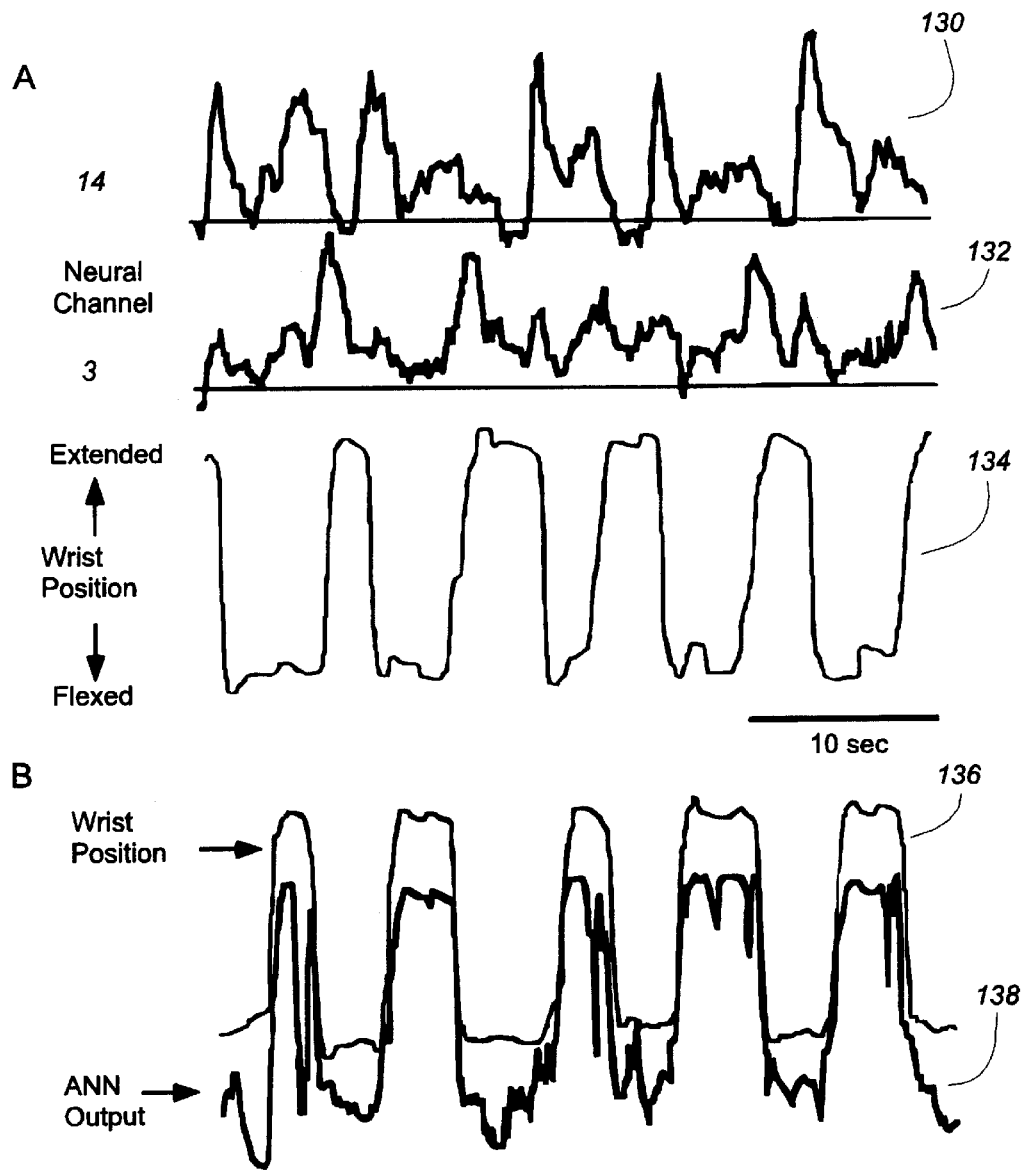
FIGS. 13(A) and (B) are graphs showing examples of processed neural discharge and the real-time prediction of wrist position from this neural discharge by the artificial neural net of FIG. 12.

An example of the success of this three-layer net in mapping two channels of neural data onto a simultaneously obtained measure of an alert monkey's wrist position, according to a preferred embodiment of the present invention, is shown in FIGS. 13(A) and 13(B). Referring first to FIG. 13(A), top two traces 130 and 132 show processed multiunit activity (outputs of S-H circuits) from two channels, identified as channel 3 and channel 14 respectively, of a 36-electrode array implanted in the left motor cortex of a trained monkey, recorded as the animal flexed and extended his right wrist. Actual wrist position is shown by a third trace 134. Channel 3 shows a peak change in activity leading wrist extension, with a smaller elevation during wrist flexion. Channel 14 shows a large increase in activity leading and during wrist flexion, and a moderate increase during extension. Referring now to FIG. 13(B), output 138 of the ANN 103, which in this case is the position of the animal's wrist predicted from activity in neural channels 3 and 14, is shown by the heavy trace adjacent to an offset lighter movement trace 136 which shows his actual wrist position. Note the good correspondence, even though only two neural channels were used to compute predicted wrist position 138. The movement trace 136 is not the same as that shown in the previous trace 134, but was computed and recorded later, during training of the ANN 103. After the ANN 103 was trained over 10 movement trials, the match between actual and predicted wrist position attained a correlation of r=0.96. Use of the ANN 103 output 138 to drive a robot "wrist" produced a robot wrist movement trace indistinguishable from the ANN 103 output 138.

Finally, referring back to FIG. 10, the output 138 of each neural net 103 is fed to an interface controller 107. An interface controller is a device which converts the output signals from one system into an appropriate set of signals for controlling some other system or device and known to persons skilled in the art. Interface controller 107 comprises a microprocessor which is programmed to convert the output of the neural net 103 into the voltages and currents that is necessary for actuating, for example, the robot controller, and thus moving the robot's wrist.

E. Calibration and Use of the System

Figure 14:
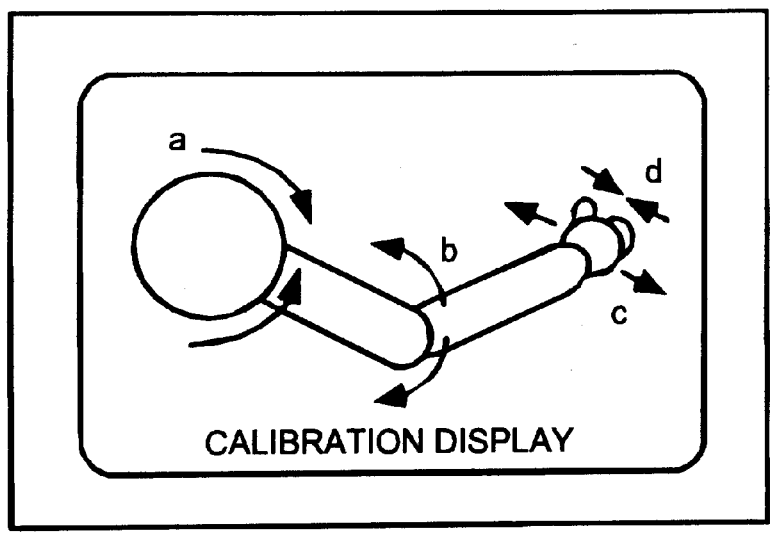
FIG. 14 is a flow chart showing steps used in calibrating the neural control system of FIG. 1, using as an example the control of an artificial limb or functional electrical stimulation of paralyzed muscles to produce a particular movement.
Figure 14:
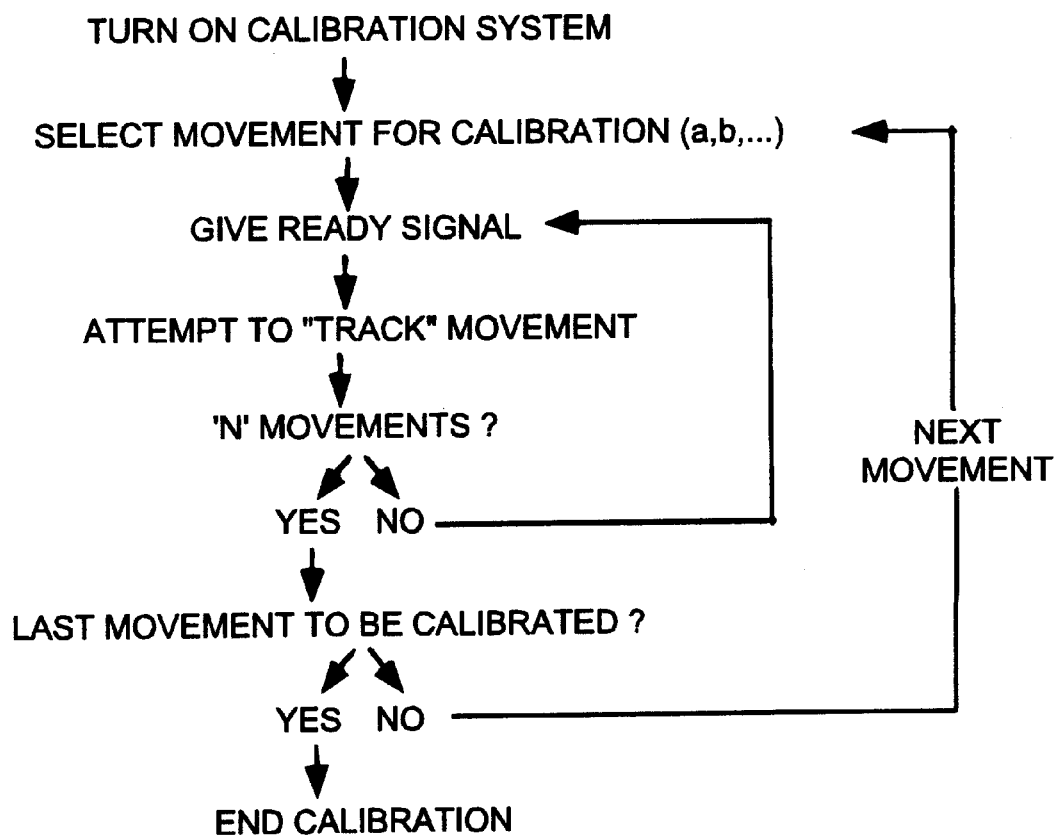

FIG. 14 shows steps that are followed by a paralyzed individual in setting up, calibrating, and using a neurally control external device according to a preferred embodiment of the present invention. Here the control of an artificial limb, or of stimulation of paralyzed muscles of the limb, to produce a particular motion is used as a particular example. It is assumed in this description that two prior conditions have been met. First, the electrodes have been implanted in brain regions that have been shown with functional imaging procedures to be under the subjects voluntary control; i.e., which are "activatable" by the subject when desired. If possible, they should also be implanted in a brain region that is normally activated when the subject attempts one or more of the particular movements that the prosthetic device will be asked to generate, though this is not an absolutely necessary requirement. Second, a prosthetic specialist will have already set channel gains and other parameters after device implantation. Each day or at selected intervals thereafter, the patient/subject would perform the following calibration routine.

First, (s)he learns to use a particular, monitored biological signal to turn on the system calibration computer when desired. If eye movements are intact, this signal could be a patterned sequence of eye blinks, sensed by a small monitoring device, that would not occur normally. If control of certain neck or facial muscles remains, their electromyographic activity could be used in the same coded way. In a totally paralyzed patient, the signal could be a particular time code of brain activity, generated voluntarily by the patient but unlike that which would occur during normal operation of the external device. A similar set of signals can be used for turning the calibration system off, or later, for turning the device to be controlled on or off when the neural control system has been calibrated.

Second, with the assistance of another person or again using a coded sequence of biological signals, the subject selects a particular movement for calibration from a predetermined list. The list may have the following options:

alternate flexion and extension of the elbow; flexion-extension of the wrist; movements about the shoulder; grasping and releasing of an object; reaching to different points in space; or some combination of these.

When the subject gives a "ready" signal, the selected movement is displayed on a video monitor, simulated by animation or a video record of a model performing an actual movement. The model movement is performed at a slow to moderate speed and, during its performance, the subject "tracks" the observed movement by attempting to move his/her own paralyzed limb in exactly the same manner and at the same speed. "N/2" repetitions would be performed, where N is a non-zero even integer. During these repetitions, the system (a) cross correlates the neural signals with the model movement(s) or some selected parameter (e.g., position, velocity, acceleration) of that movement; and (b) on the basis of the average of these correlations over the N/2 repetitions, determines which subset of neural channels was most highly correlated with the model movement and its parameters. The activity on the selected subset channels would then (c) be routed to the ANNs 103 which control the components of the external device that will produce a movement like the model movement. Another N/2 repetitions are then performed, and the appropriate ANNs 103 (d) "map" these selected neural inputs onto a stored record of parameter values for the model movement.

The subject now performs this same procedure for the next movement in the set, and the four steps (a) through (d) are repeated for that movement. And so on, until the entire calibration procedure has been performed. This procedure is performed daily or only at needed intervals (when the subject notices a diminution in control accuracy), with the optimal neural channels being reselected at each calibration procedure and mapped again onto the desired movement functions. Thus, this periodic calibration procedure adapts to or allows compensation for changing neural signal parameters, and it ensures the optimal selection of those channels that are still useful at any time for device control.

Please note also that the subject's own brain can also adapt to changing signal properties and the challenges that these changes impose on device control. That is, if the subject can voluntarily activate the brain region from which signals are monitored and can vary these signal levels, then (s)he can learn to modulate these activation levels so that the external device can still be manipulated, even if there is drift or other unknown changes in the activity of the recorded neural channels.

Obviously, many modifications and variations of the present invention are possible to persons skilled in the art, without departing from the spirit and the scope of the invention disclosed herein. It is to be understood, therefore, that the invention can be practiced otherwise than as specifically described.

What is claimed is:

1. A device for collecting multicellular signals directly from a central nervous system and transmitting the signals to an external receiver, comprising:
   A) a plurality of electrodes formed in bundles of flexible wires with tips at staggered length aligned to be implanted in the central nervous system, each electrode for collecting multicellular signals from the central nervous system; and
   B) a signal processing mechanism connected to the electrodes for multiplexing and transmitting the signals from the electrodes to the external receiver;
   wherein the tips of the electrodes are sized to have a recording area greater than 400 $\mu m^2$ for collecting the multicellular signals from the central nervous system.

2. The device according to claim 1, wherein the number of the flexible wires in a bundle ranges from 3 to 10.

3. The device according to claim 1, wherein the diameter of the flexible wires is smaller than 50 $\mu m$.

4. The device according to claim 1, wherein the difference in length from one tip to its neighbor tip of the wires is variable.

5. The device according to claim 4, wherein the difference in length from one tip to its neighbor tip of the wires is about 0.3 to 0.6 mm.

6. The device according to claim 1, wherein the flexible wires in a bundle are made from noble metal.

7. The device according to claim 1, wherein the signal processing mechanism comprises:
   A) an insulating substrate;
   B) an array of electrode contact pads mounted on the substrate for receiving the electrodes, each electrode received individually by one of the electrode contact pads, and with the electrode contact pads being electrically isolated from each other at the substrate;
   C) a microchip bonded in close contact with the substrate for receiving and multiplexing the signals from the electrodes; and
   D) an electric connection to the microchip for relaying power to the microchip and transmitting the signals received at the microchip to the external receiver.

8. The device according to claim 7, wherein the electric connection is a hardware device.

9. The device according to claim 8, wherein the hardware device is a cable.

10. The device according to claim 7, wherein the electric connection is a wireless device.

11. The device according to claim 10, wherein the wireless device is a nonresonant wireless setup.

12. The device according to claim 11, wherein the nonresonant wireless setup comprises:
    A) a first coil in connection with the microchip for relaying power to the microchip; and
    B) a second coil in connection with the microchip for receiving and transmitting the multiplexed signals to the external receiver.

13. The device according to claim 10, wherein the wireless device is a resonant wireless setup.

14. The device according to claim 13, wherein the resonant wireless setup comprises:
    A) a coil in connection with the microchip for relaying power to the microchip; and
    B) a low pass filter in connection with the microchip for receiving and transmitting the multiplexed signals to the external receiver.

15. The device according to claim 7, wherein the microchip comprises signal processing integrated circuits.

16. An apparatus for recording multi-neuron signals directly from a central nervous system, comprising: a plurality of sensors, wherein each sensor further comprises a bundle of noble metal wires with tips at staggered lengths and with the tips sized to have a recording area greater than 400 $\mu m^2$ so that each tip collects multicellular signals from the central nervous system.

17. An instrument for collecting multicellular signals directly from a central nervous system and transmitting the signals to an external receiver, comprising:
    A) at least one sensor for receiving the signals, wherein the sensor comprises:
       i) a bundle of wires of staggered lengths arranged in an array, wherein each wire has a tip for receiving multicellular signals from the central nervous system; and ii) an optical cement bead through which the wires pass for holding the wires in position in a selected distance from the most distant wire tip; and B) a signal processor connected to the sensor for multiplexing and transmitting the signals from the sensor to the external receiver;

wherein the signal processor conducts adaptive processing of the signals from the sensor so that the instrument responds to changes in the multicellular signals.

18. The instrument according to claim 17, wherein the selected distance is about 6–8 mm.

19. The instrument according to claim 17, wherein the wires are made from conductive materials.

20. The instrument according to claim 17, wherein the conductive materials are noble metal.

21. A channel display system for monitor recorded multicellular signals, comprising:

A) a device for recording multichannel neural signals directly from a central nervous system and broadcasting the signals, wherein the device has electrodes with staggered tips, each electrode is sized to have a surface area greater than 400 $\mu m^2$, and each electrode is for detecting multicellular signals;

B) an external receiver for receiving the multicellular signals;

C) electric connection means for connecting to an external receiver to relay the signals; and D) a visual display for displaying the signals in a matrix, wherein each cell of the matrix represents a separate neural data channel.

22. The channel display system according to claim 21, wherein the visual display comprises an LED, wherein the intensity of illumination of the LED is a positive function of the level of neural signals fed from the related neural data channel.

23. The channel display system according to claim 21, wherein the visual display comprises a computer screen, wherein the color of each cell of the display matrix on the screen is coded according to the level of neural signals fed from the related neural data channel.

24. A system for collecting multicellular signals directly from a central nervous system and for transmitting processed signals to a device, comprising:

a sensor for detecting multicellular signals directly from the central nervous system, the sensor having a plurality of electrodes for being implanted near the central nervous system to allow for chronic detection of the multicellular signals, each electrode for detecting multicellular signals from the central nervous system; and an interface for receiving the multicellular signals from the sensor, for processing the multicellular signals to generate processed signals, and for transmitting the processed signals to the device; and the device for receiving the processed signals;

wherein the interface conducts adaptive processing of the multicellular signals so that the system responds to changes in the multicellular signals.

25. The system as set forth in claim 24, wherein the sensor is for being implanted into the brain.

26. The system as set forth in claim 24, wherein the device delivers the processed signals to a prosthetic device.

27. The system as set forth in claim 24, wherein the device delivers the processed signals to muscular tissue.

28. The system as set forth in claim 24, wherein the device is a prosthetic device.

29. The system as set forth in claim 24, wherein the electrodes of the sensor are formed of noble metal.

30. The system as set forth in claim 24, wherein the electrodes comprise wires and the sensor comprises a wire bundle.

31. The system as set forth in claim 24, wherein the electrodes are mounted to a substrate.

32. The system as set forth in claim 24, wherein the sensor is for being implanted into a skull and the interface is connected to the sensor through the skull.

33. The system as set forth in claim 24, wherein the sensor is for being implanted into a skull and the interface is located entirely external to the skull and is coupled to the sensor through a wireless connection.

34. The system as set forth in claim 24, wherein the interface processes the signals for controlling the device.

35. The system as set forth in claim 24, further comprising a movement calibration system for calibrating the multicellular signals with movement of the device.

36. The system as set forth in claim 24, wherein the interface includes a neural network.

37. The system as set forth in claim 36, wherein the neural network comprises an artificial neural network.

38. The system as set forth in claim 24, wherein the interface maps the multicellular signals onto an output parameter.

39. The system as set forth in claim 38, wherein the interface comprises a neural network.

40. The system as set forth in claim 24, wherein the interface shapes the processed signal for control of the device.

41. The system as set forth in claim 40, wherein the interface comprises a neural network.

42. The system as set forth in claim 41, wherein the interface further includes an interface controller for receiving an output of the neural network.

* * * * *

UNITED STATES PATENT AND TRADEMARK OFFICE
CERTIFICATE OF CORRECTION

PATENT NO. : 6,171,239 B1
DATED : January 9, 2001
INVENTOR(S) : Donald R. Humphrey It is certified that error appears in the above-identified patent and that said Letters Patent is hereby corrected as shown below:

<u>Column 1,</u>
Line 5, please insert the following:
-- The subject matter of the present invention was supported in part by grant from the United States National Institute of Health Grant No. NS12308. --

Signed and Sealed this

Twelfth Day of July, 2005

JON W. DUDAS
*Director of the United States Patent and Trademark Office*

US006171239C1

(12) EX PARTE REEXAMINATION CERTIFICATE (4962nd)
United States Patent
Humphrey

(10) Number: US 6,171,239 C1
(45) Certificate Issued: Jul. 13, 2004

(54) SYSTEMS, METHODS, AND DEVICES FOR CONTROLLING EXTERNAL DEVICES BY SIGNALS DERIVED DIRECTLY FROM THE NERVOUS SYSTEM

(75) Inventor: Donald R. Humphrey, Atlanta, GA (US)

(73) Assignee: Emory University, Atlanta, GA (US)

Reexamination Request:
No. 90/006,368, Aug. 30, 2002

Reexamination Certificate for:
Patent No.: 6,171,239
Issued: Jan. 9, 2001
Appl. No.: 09/135,249
Filed: Aug. 17, 1998

(51) Int. Cl.[7] ................................................ A61B 5/04
(52) U.S. Cl. ...................... 600/372; 600/378; 600/544; 607/116

(56) References Cited

U.S. PATENT DOCUMENTS

| | | |
|---|---|---|
| 3,837,339 A | 9/1974 | Aisenberg et al. |
| 3,850,161 A | 11/1974 | Liss |
| 4,055,175 A | 10/1977 | Clemens et al. |
| 4,146,029 A | 3/1979 | Ellinwood, Jr. |
| 4,294,245 A | 10/1981 | Bussey |
| 4,360,031 A | 11/1982 | White |
| 4,461,304 A | 7/1984 | Kuperstein |
| 4,633,889 A | 1/1987 | Talalla et al. |
| 4,690,142 A | 9/1987 | Ross et al. |
| 4,865,048 A | 9/1989 | Eckerson |
| 4,878,913 A | 11/1989 | Aebischer et al. |
| 4,883,666 A | 11/1989 | Sabel et al. |
| 5,037,376 A | 8/1991 | Richmond et al. |
| 5,081,990 A | 1/1992 | Deletis |
| 5,119,832 A | 6/1992 | Xavier |
| 5,156,844 A | 10/1992 | Aebischer et al. |
| 5,215,088 A | 6/1993 | Normann et al. |
| 5,325,865 A | 7/1994 | Beckman et al. |
| 5,361,760 A | 11/1994 | Normann et al. |
| 5,423,877 A | 6/1995 | Mackey |
| 5,458,631 A | 10/1995 | Xavier |
| 5,474,547 A | 12/1995 | Aebischer et al. |
| 5,617,871 A | 4/1997 | Burrows |
| 5,638,826 A | 6/1997 | Wolpaw et al. |
| 5,687,291 A | 11/1997 | Smyth |
| 5,692,517 A | 12/1997 | Junker |
| 5,697,951 A | 12/1997 | Harpstead et al. |
| 5,713,923 A | 2/1998 | Ward et al. |
| 5,735,885 A | 4/1998 | Howard, III et al. |
| 5,758,651 A | 6/1998 | Nygard et al. |
| 5,797,898 A | 8/1998 | Santini, Jr. et al. |
| 5,843,093 A | 12/1998 | Howard, III |
| 5,843,142 A | 12/1998 | Sultan |
| 5,855,801 A | 1/1999 | Lin et al. |

(List continued on next page.)

OTHER PUBLICATIONS

Nicolelis, Miguel A.L., "Trigeminal System Plasticity During Facial Anethesia," Department of Health and Human Services, Public Health Service, Grant No. 2 R01 DE11451–05, Including Summary Statement, Oct., 1997.

(List continued on next page.)

*Primary Examiner*—Lee Cohen

(57) ABSTRACT

A system and method control prostheses and other devices with signals received by sensors implanted directly in the brain or other parts of the nervous system of a subject/patient and transmitted to an external receiver. Included in the system are sensors in the form of bundles of small, insulated, flexible wires, configured in a parallel or twisted array, which are used to receive multicellular signals from small clusters of neurons. A new "calibration/adaptation" system is developed, in which the neural signals are cross-correlated with the parameters of a set of standardized or model movements as the subject/patient attempts to emulate the model movements, and on the basis of the correlations the neural signals that are best suited for control of the corresponding movement or movement parameter of the external device are selected. Periodic use of this calibration system compensates for or adapts to uncontrolled changes in neural signal parameters over time, and therefore results in re-selection of the optimal neural channels for better device control. Artificial neural nets are used for mapping the selected neural signals onto appropriate movements or control parameters of the external device.

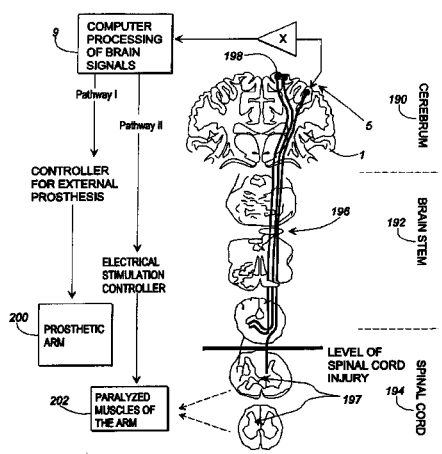

U.S. PATENT DOCUMENTS

| | | |
|---|---|---|
| 5,873,840 A | 2/1999 | Neff |
| 5,928,228 A | 7/1999 | Kordis et al. |
| 5,938,688 A | 8/1999 | Schiff |
| 5,938,689 A | 8/1999 | Fischell et al. |
| 5,938,690 A | 8/1999 | Law et al. |
| 6,001,065 A | 12/1999 | DeVito |
| 6,006,124 A | 12/1999 | Fischell et al. |
| 6,016,449 A | 1/2000 | Fischell et al. |
| 6,024,700 A | 2/2000 | Nemirovski et al. |
| 6,024,702 A | 2/2000 | Iversen |
| 6,027,456 A | 2/2000 | Feler et al. |
| 6,038,477 A | 3/2000 | Kayyali |
| 6,061,593 A | 5/2000 | Fischell et al. |
| 6,086,582 A | 7/2000 | Altman et al. |
| 6,092,058 A | 7/2000 | Smyth |
| 6,113,553 A | 9/2000 | Chubbuck |
| 6,125,300 A | 9/2000 | Weijand et al. |
| 6,128,538 A | 10/2000 | Fischell et al. |
| 6,134,474 A | 10/2000 | Fischell et al. |
| 6,154,678 A | 11/2000 | Lauro |
| 6,161,045 A | 12/2000 | Fischell et al. |
| 6,163,725 A | 12/2000 | Peckham et al. |
| 6,169,981 B1 | 1/2001 | Werbos |
| 6,171,239 B1 | 1/2001 | Humphrey |
| 6,175,762 B1 | 1/2001 | Kirkup et al. |
| 6,181,965 B1 | 1/2001 | Loeb et al. |
| 6,185,455 B1 | 2/2001 | Loeb et al. |
| 6,216,045 B1 | 4/2001 | Black et al. |
| 6,224,549 B1 | 5/2001 | Drongelen |
| 6,240,315 B1 | 5/2001 | Mo et al. |
| 6,254,536 B1 | 7/2001 | DeVito |
| 6,263,237 B1 | 7/2001 | Rise |
| 6,280,394 B1 | 8/2001 | Maloney et al. |
| 6,313,093 B1 | 11/2001 | Frey, II |
| 6,319,241 B1 | 11/2001 | King et al. |
| 6,353,754 B1 | 3/2002 | Fischell et al. |
| 6,354,299 B1 | 3/2002 | Fischell et al. |
| 6,358,202 B1 | 3/2002 | Arent |
| 6,360,122 B1 | 3/2002 | Fischell et al. |
| 6,427,086 B1 | 7/2002 | Fischell et al. |
| 6,436,708 B1 | 8/2002 | Leone et al. |
| 6,459,936 B2 | 10/2002 | Fischell et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 2001/0023368 A1 | 9/2001 | Black et al. |
| 2001/0027336 A1 | 10/2001 | Gielen et al. |
| 2001/0029391 A1 | 10/2001 | Gluckman et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0013612 A1 | 1/2002 | Whitehurst |
| 2002/0016638 A1 | 2/2002 | Mitra et al. |
| 2002/0099412 A1 | 7/2002 | Fischell et al. |
| 2002/0169485 A1 | 11/2002 | Pless et al. |
| 2003/0083716 A1 | 5/2003 | Nicolelis et al. |
| 2003/0093129 A1 | 5/2003 | Nicolelis et al. |

OTHER PUBLICATIONS

Nicolelis, Miguel A.L., "Trigeminal System Plasticity During Facial Anethesia," Department of Health and Human Services, Public Health Service, Grant No. 2 R01 DE11451–06, Apr., 1999.

Nicolelis, Miguel A.L., "Trigeminal System Plasticity During Facial Anethesia," Department of Health and Human Services, Public Health Service, Grant No. 2 R01 DE11451–07, Apr., 2000.

Nicolelis, Miguel A.L., "Trigeminal System Plasticity During Facial Anethesia," Department of Health and Human Services, Public Health Service, Grant No. 2 R01 DE11451–08, Apr. 2001.

Nicolelis, Miguel A.L., "Trigeminal System Plasticity During Facial Anethesia," Department of Health and Human Services, Public Health Service, Grant No. 2 R01 DE11451–09, Apr., 2002.

Nicolelis, Miguel A.L., "Corticofugal Modulation of Tactile Sensory Processing," Department of Health and Human Services, Public Health Service, National Institute of Dental and Craniofacial Research of the Nationsl Institutes of Health, Grant No. 1 R01 DE013810–01 A1, Jun., 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of Health, Grant No. 5 R01 DE013810–02, Mar., 2002.

International Publication No. WO 03/035165, May 1, 2003, Nicolelis et al.

International Publication No. WO 03/037231, May 8, 2003, Nicolelis et al.

Miguel A. L. Nicolelis, "Brain–machine interfaces to restore motor function and probe neural circuits," Nature Reviews, Neuroscience, vol. 4, May 2003, pp 417–422.

Kensall D. Wise et al., "An Integrated–Circuit Approach to Extraceullar Microelectrodes," IEEE Transactions on Biomedical Engineering, vol. BME–17, No. 3. Jul. 1970, pp 238–247.

Donald R. Humphrey et al., "Predicting Measures of Motor Performance from Multiple Cortical Spike Trains," Science, New Series, vol. 170, Issue 3959, Nov. 13, 1970, pp 758–762.

A. Bohg, "Ethylene Diamine–Pyrocatechol–Water Mixture Shows Etching Anomaly in Boron–Doped Silicon," Journal of the Electrochemical Society, vol. 118, No. 2, Feb. 1971, pp 401–402.

Donald R. Humphrey, "Relating Motor Cortex Spike Trains to Measures of Motor Performance," Department of Physiology, Emory University, Brain Research, No. 40, 1972, pp 7–18.

Arnold Starr et al., "An Evaluation of Photoengraved Microelectrodes for Extracellular Single–Unit Recording," IEEE Transactions on Biomedical Engineering, vol. BME–20, No. 4, Jul. 1973, pp 291–293.

Kensall D. Wise et al., "A Low–Capacitance Multielectrode Probe for Use in Extracellular Neurophysiology," IEEE Transactions on Biomedical Engineering, vol. BME–22, No. 3, May 1975, pp 212–219.

V. B. Mountcastle et al., "Posterior Parietal Association Cortex of the Monkey: Command Functions for Operations Within Extrapersonal Space," The Journal of Neurophysiology, vol. 38, No. 4, 1975, pp 871–908.

Edward M. Schmidt, "Single Neuron Recording from Motor Cortex as a Possible Source of Signals for Control of External Devices," Annals of Biomedical Engineering, vol. 8, 1980, pp 339–349.

Spencer L. BeMent, et al., "Solid–State Electrodes for Multichannel Multiplexed Intracortical Neuronal Recording," IEEE Transactions on Biomedical Engineering, vol. BME–33 No. 2, Feb. 1986, pp 230–241.

Apostolos P. Georgopoulos et al., "Neuronal Population Coding of Movement Direction," Science, vol. 233, Sep. 26, 1986, pp 1416–1419.

Kenneth L. Drake et al., "Performance of Planar Multisite Microprobes in Recording Extracellular Single–Unit Intraortical Activity," IEEE Transactions on Biomedical Engineering, vol. 35, No. 9, Sep. 1988, pp 719–732.

Patrick K. Campbell et al., "A chronic intracortical electrode array: Preliminary results," Journal of Biomed. Material Res.: Applied Biomaterials, vol. 23, No. 2, 1989, pp 245–259.

Andrew R. Mitz et al., "Learning–dependent Neuronal Activity in the Premotor Cortex: Activity during the Acquisition of Conditional Motor Associations," The Journal of Neuroscience, vol. 11, No. 6, Jun. 1991, pp 1855–1872.

Patrick K. Campbell et al., "A Silicon–Based, Three–Dimensional Neural Interface: Manufacturing Processes for an Intracortical Electrode Array," IEEE Transactions, 1991, pp 758–768.

A. C. Hoogerwerf et al., "A Three–Dimensional Neural Recording Array," IEEE Transactions, 1991, pp 120–123.

Gregory T. A. Kovacs et al., "Regeneration Microelectrode Array for Peripheral Nerve Recording and Stimulation," Transactions on Biomedical Engineering, vol. 39, No. 9, Sep. 1992, pp 893–902.

Kelly E Jones et al., "A Glass/Silicon Composite Intracortical Electrode Array," Annals of Biomedical Engineering. vol. 20, 1992, pp 423–437.

Reinhard Eckhorn et al., "A new method for the insertion of multiple microprobes into neural and muscular tissue, including fiber electrodes, fine wires, needles and microsensors," Journal of Neuroscience Methods, vol. 49, 1993, pp. 175–179.

Craig T. Nordhausen et al., "Optimizing recrding capabilities of the Utah Intracortical Electrode Array," Brain Research, vol. 637, Nos. 1/2, Feb. 21, 1994, pp 27–36.

Jamille F. Hetke et al., "Silicon Ribbon Cables for Chronically Implantable Microelectrode Arrays," IEEE Transactions on Biomedical Engineering, vol. 41, No. 4, Apr. 1994, pp 314–321.

Arnold C. Hoogerwerf et al., "A Three–Dimensional Microelectrode Array for Chronic Neural Recording," IEEE Transactions on Biomedical Engineering, vol. 41, No. 12, Dec. 1994, pp 1136–1146.

Camilo Toro et al., "8–12 Hz rhythmic oscillations in human motor cortex during two–dimensional arm movements: evidence for representation of kinematic parameters," Departments of Neurology, Neurosurgery, and Physiology, University of Minnesota; MINCEP Epilepsy Care, P.A.; The Minnesota Epilepsy Group of United and St. Paul Children's Hospital; and Human Motor Control Section, National Institute of Neurological Disorders and Stroke, National Institutes of Health, Electroencephalography and Clnical Neurophysiology, No. 93, 1994, pp 390–403.

Miguel A. L. Nicolelis et al., "Sensorimotor Encoding by Synchronous Neural Ensemble Activity at Multiple Levels of the Somatosensory System," Science, vol. 268, Jun. 2, 1995, pp 1353–1358.

Jerome N. Sanes et al., "Shared Neural Substrates Controlling Hand Movements in Human Motor Cortex," Science, vol. 268, Jun. 23, 1995, pp 1775–1777.

D. M. Halliday et al., "A Framework for the Analysis of Mixed Time Series/Point Process Data–Theory and Application to the Study of Physiological Tremor, Single Motor Unit Discharges and Electromyograms," Progress in Biophysics Molecular Biology, vol. 64, Nos. 2/3, 1995, pp 237–278.

Qing Bai et al., "A High–Yield Process for Three–Dimensional Microelectrode Arrays," Solid–State Sensor and Actuator Workshop, Hilton Head, South Carolina, Jun. 2–6, 1996, pp 262–265.

Changhyun Kim et al., "A 64–Site Multishank CMOS Low–Profile Neural Stimulating Probe," IEEE Journal of Solid–State Circuits, vol. 31, No. 9, Sep. 1996, pp 1230–1238.

Gwo–Ching Chang et al., "Real–time implementation of electromyogram pattern recognition as a control command of man–machine interface," Medical Engineering Phys., vol. 18, No. 7, 1996, pp 529–537.

P. Nisbet, "Integrating assistive technologies: current practices and future possibilities," Med. Eng. Phys., vol. 18, No. 3, 1996, pp 193–202.

TR Scott et al., "The Monitoring of Tendon Tension with an Implantable Intratendon Probe and its Use in the Control of Neuroprostheses," IEEE Transactions on Rehabilitation Engineering, vol. 5, No. 2, Jun. 1997, pp. 233–235.

Barbara M. Faggin et al., "Immediate and simultaneous sensory reorganization at cortical and subcortical levels of the somatosensory system," Proc. Natl. Acad. Science USA, vol. 94, Aug. 1997, pp 9428–9433.

Robert M. Bradley et al., "Long term chronic recordings from peripheral sensory fibers using a sieve electrode array," Journal of Neuroscience Methods, vol. 73, 1997, pp 177–186.

David K. Warland et al., "Decoding Visual Information From a Population of Retinal Ganglion Cells," The American Physiological Society, 1997, pp 2336–2350.

Steven P. Wise et al., "Premotor and Parietal Cortex: Cortiococortical Connectivity and Combinatorial Computations," Annual Review of Neuroscience, vol. 20, 1997, pp 25–42.

P. R. Kennedy et al., "Restoration of Neural outpur from a paralyzed patient by a direct brain connection," NeuroReport, vol. 9. No. 8, Jun. 1998 pp 1707–1711.

Paolo Dario et al., "Neural Interfaces for Regenerated Nerve Stimulation and Recording," IEEE Transactions on Rehabilitation Engineering, vol. 6, No. 4, Dec. 1998, pp 353–363.

Nicholas G. Hatsopoulos et al., "Information about movement direction obtained from synchronous activity of motor cortical neurons," Proc. Natl. Acad. Sci. USA, vol. 95, Dec. 1998, pp 15706–15711.

John P. Donoghue et al., "Neural Discharge and Local Field Potential Oscillations in Primate Motor Cortex During Voluntary Movements," The American Physiological Society, 1998, pp 159–173.

Gregor Rainer et al., "Prospective Coding for Objects in Primate Prefrontal Cortex," The Journal of Neuroscience, vol. 19, No. 13, Jul. 1, 1999, pp 5493–5505.

John K. Chapin et al., "Real–time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, p 664–670.

E. M. Maynard et al., "Neuronal Interactions Improve Cortical Population Coding of Movement Direction," The Journal of Neuroscience, vol. 19, No. 18, Sep. 15, 1999, pp. 8083–8093.

F. Gandolfo et al., "Cortical correlates of learning in monkeys adapting to a new dynamical environment," PNAS, vol. 97, No. 5, Feb. 29, 2000, pp 2259–2263.

J. F. Marsden et al., Organization of Cortical Activities Related to Movement in Humans, The Journal of Neuroscience, vol. 20, No. 6, Mar. 15, 2000, pp 2307–2314.

D. Gareth Evans et al., "Controlling Mouse Pointer Position Using an Infrared Head–Operated Joystick," IEEE Transactions on Rehabilitation Engineering, vol. 8, No. 1, Mar. 2000, pp 107–117.

Qing Bai et al., "A High–Yield Microassembly Structure For Three–Dimensional Microelectrode Arrays," IEEE Transactions on Biomedical Engineering, vol. 47, No. 3, Mar. 2000, pp 281–289.

Jonathan R. Wolpaw et al., "Brian–Computer Interface Technology: A Review of the First International Meeting," IEEE Transactions on Rehabilitation Engineering, vol. 8, No. 2, Jun. 2000, pp 164–173.

Simon P. Levine et al., "A Direct Brain Interface Based on Event–Related Potentials," IEEE Transactions on Rehabilitation Engineering, vol. 8, No. 2, Jun. 2000 pp 180–185.

Robert E. Isaacs et al., "Work Toward Real–Time Control of a Cortical Neural Prothesis," IEEE Transactions on Rehabilitation Engineering, vol. 8, No. 2, Jun. 2000 pp 196–198.

Scott Makeig et al., A Natural Basis for Efficient Brain–Actuated Control, IEEE Transactions on Rehabilitation Engineering, vol. 8, No. 2, Jun. 2000, pp 208–211.

Johan Wessberg et al., "Real–time prediction of hand trajectory by ensembles of cortical neurons in primates," Nature, vol. 408, Nov. 16, 2000, pp 361–365.

Jerome N. Sanes et al., "Plasticity and Primary Motor Cortex," Annual Reviews, Neuroscience, Brown University Library, vol. 23, 2000, pp 393–415.

Jonathan C. Jarvis et al., "The application and technology of implantable neuromuscular stimulators: an introduction and overview," Medical Engineering & Physics, No. 23, Jan. 11, 2001, pp 3–7.

Miguel A. L. Nicolelis, "Real–time direct interfaces between the brain and electronic and mechanical devices could one day be used to restore sensory and motor functions lost through injury or disease. Hybrid brain–machine interfaces also have the potential to enhance our perceptual, motor and cognitive capabilities by revolutionizing the way we use computers and interact with remote environments," Nature, vol. 409, Jan. 18, 2001, pp 403–407.

Gerald E. Loeb et al., BION™ system for distributed neural prosthetic interfaces, Medical Engineering & Physics, vol. 23, Jan. 26, 2001, pp 9–18.

Patrick J. Rousche et al., "Flexible Polyimide–Based Intracortical Electrode Arrays with Bioactive Capability," IEEE Transactions on Biomedical Engineering, vol. 48, No. 3, Mar. 2001, pp 361–371.

Qing Bai et al., "Single–Unit Neural Recording with Active Microelectrode Arrays," IEEE Transactions on Biomedical Engineering, vol. 48, No. 8, Aug. 2001, pp 911–920.

David L. Zealear et al., The Biocompatibility, Integrity, and Positional Stability of an Injectable Microstimulator for Reanimation of the Paralyzed Larynx, IEEE Transactions on Biomedical Engineering, vol. 48, No. 8, Aug. 2001, pp 890–897.

Dawn M. Taylor et al., Using Virtual Reality to Test the Feasibility of Controlling an Upper Limb Fes System Directly from Multiunit Activity in the Motor Cortex, Arizona State University; and The Neurosciences Institute, Summer 2001, pp 1–3.

Ranu, Jung et al., "Real–Time Interaction Between a Neuromorphic Electronic Circuit and the Spinal Cord," IEEE Transactions on Neural Systems and Rehabilitation Engineering, vol. 9, No. 3, Sep. 2001, pp 319–326.

Shay Shoham, "Advances Towards an Implantable Motor Cortical Interface," The University of Utah, Dec. 2001, pp 1–157.

John K. Chapin et al., "Neural Prostheses for Restoration of Sensory and Motor Function," CRC Press, LLC, 2001, Chapters 6, 8 and 9, pp 179–219, pp 235–261, pp 263–283.

Andrew B. Schwartz et al., "Extraction algorithms for cortical control of arm prosthetics," The Neuroscience Institute; and Department of Bioengineering, Arizona State University, 2001, pp 701–707.

István Ulbert et al., "Multiple microelectrode–recording system for human intracortical applications," Journal of Neuroscience Methods, vol. 106, 2001, pp 69–79.

Mijail D. Serruya et al., "Instant Neural Control of a Movement Signal," Nature, vol. 416, mar. 14, 2002, pp. 141–142.

Dawn M. Taylor et al., "Direct Cortical Control of 3D Neuroprosthetic Devices," Science, vol. 296, Jun. 7, 2002, pp 1829–1832.

John P. Donoghue, "Connecting cortex to machines: recent advances in brain interfaces," Nature Neuroscience Supplement, vol. 5, Nov. 2002, pp 1085–1088.

Y. Gao, et al., "Probabilistic Inference of Hand Motion from Neural Activity in Motor Cortex," In Advances in Neural Information Processing Systems 14, The MIT Press, 2002, pp 1–8.

Mijail Serruya et al., "Robustness of neuroprosthetic decoding algorithms," Biological Cybernetics, 2003, pp 1–10.

Nicolelis et al., "Reconstructing the Engram: Simultaneous, Multisite, Many Single Neuron Recordings," Neuron, p. 529–537, (Apr. 1997).

Owens et al., "Multi–electrode Array for Measuring Evoked Potentials from Surface of Ferret Primary Auditory Cortex," Journal of Neuroscience Methods, p. 209–220, (May 1995).

Nicolelis et al., "Spatiotemporal Structure of Somatosensory Responses of Many–Neuron Ensembles in the Rat Ventral Posterior Medial Nucleus of the Thalamus," Journal of Neuroscience, p. 3511–3532, (Jun. 1994).

Nicolelis et al., "Induction of Immediate Spatiotemporal Changes in Thalamic Networks by Peripheral Block of Ascending Cutaneous Information," Nature, p. 533–536, (Feb. 1993).

Summerlee et al., "The Effect of Behavioural Arousal on the Activity of Hypthlamic Neurons in Unanaesthetized, Freely Moving Rats and Rabbits," Proceedings of the Royal Society of London Series B–Biological Sciences, p. 263–272, (Jan. 1982).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 17–20 and 24–42 is confirmed.

Claims 1, 7, 16, 21 and 22 are determined to be patentable as amended.

Claims 2–6, 8–15 and 23, dependent on an amended claim, are determined to be patentable.

New claims 43–243 are added and determined to be patentable.

1. A device for collecting multicellular signals directly from a central nervous system and transmitting the signals to an external receiver, comprising:
   A) a plurality of electrodes formed in bundles of flexible wires with tips at staggered length aligned to be implanted in the central nervous system, each electrode for collecting multicellular signals from the central nervous system; [and]
   B) a signal processing mechanism connected to the electrodes for multiplexing and transmitting the signals from the electrodes to the external receiver; *and*
   *C) a movement calibration system for calibrating the collected multicellular signals with movement of an external unit;*
   wherein the tips of the electrodes are sized to have a recording area greater than 400 $\mu m^2$ for collecting the multicellular signals from the central nervous system.

7. [The] *A* device [according to claim 1,] *for collecting multicellular signals directly from a central nervous system and transmitting the signals to an external receiver comprising:*
   *A) a plurality of electrodes formed in bundles of flexible wires with tips at staggered length aligned to be implanted in the central nervous system, each electrode for collecting multicellular signals from the central nervous system; and*
   *B) a signal processing mechanism connected to the electrodes for multiplexing and transmitting the signals from the electrodes to the external receiver;* wherein the signal processing mechanism comprises:
   [A] *i)* an insulating substrate;
   [B] *ii)* an array of electrode contact pads mounted on the substrate for receiving the electrodes, each electrode received individually by one of the electrode contact pads, and with the electrode contact pads being electrically isolated from each other at the substrate;
   [C] *iii)* a microchip bonded in close contact with the substrate for receiving and multiplexing the signals from the electrodes; and
   [D] *iv)* an electric connection to the microchip for relaying power to the microchip and transmitting the signals received at the microchip to the external receiver;
   wherein the tips of the electrodes are sized to have a recording area greater than 400 $\mu m^2$ for collecting the multicellular signals from the central nervous system.

16. An apparatus for recording multi-neuron signals directly from a central nervous system, comprising:
    a plurality of sensors, wherein each sensor further comprises a bundle of noble metal wires with tips at staggered lengths and with the tips sized to have a recording area greater than 400 $\mu m^2$ so that each tip collects multicellular signals from the central nervous system; *and*
    *a movement calibration system for calibrating the collected multicellular signals with movement of a device.*

21. A channel display system for [monitor] *monitoring* recorded multicellular signals, comprising:
    A) a device for recording multichannel neural signals directly from a central nervous system and broadcasting the signals, wherein the device has electrodes with staggered tips, each electrode is sized to have a surface area greater than 400 $\mu m^2$, and each electrode is for detecting multicellular signals;
    B) an external receiver for receiving the multicellular signals *from the device*;
    C) electric connection means for connecting *the device* to [an] *the* external receiver to relay the signals; [and]
    D) a visual display for displaying the signals in a matrix, wherein each cell of the matrix represents a separate neural data channeli ; and
    *E) a movement calibration system for calibrating the detected multicellular signals with movement of an attached unit.*

22. [The] *A* channel display system [according to claim 21,] *for monitoring recorded multicellular signals, comprising:*
    *A) a device for recording multichannel neural signals directly from a central nervous system and broadcasting the signals, wherein the device has electrodes with staggered tips, each electrode is sized to have a surface area greater than 400 $\mu m^2$, and each electrode is for detecting multicellular signals;*
    *B) an external receiver for receiving the multicellular signals from the device;*
    *C) electric connection means for connecting the device to the external receiver to relay the signals; and*
    *D) a visual display for displaying the signals in a matrix, wherein each cell of the matrix represents a separate neural data channel, and* wherein the visual display comprises an LED, wherein the intensity of illumination of the LED is a positive function of the level of neural signals fed from the related neural data channel.

43. *The system of claim 24, wherein the central nervous system is included in a body, and at least a portion of the device is configured to be external the body.*

44. *The system of claim 43, wherein the device includes a computer.*

45. *The system of claim 43, wherein the device includes a computer display.*

46. *The system of claim 43, wherein the device includes an artificial limb.*

47. *The system of claim 43, wherein the device includes a robotic component.*

48. The system of claim 24, wherein the device delivers the processed signals to a computer.

49. The system of claim 24, wherein the device delivers the processed signals to a computer display.

50. The system of claim 24, wherein the device includes a computer.

51. The system of claim 26, wherein the device includes a computer.

52. The system of claim 24, wherein the device includes a computer display.

53. The system of claim 24, wherein the sensor includes signal processing circuitry.

54. The system of claim 53, wherein the signal processing circuitry includes an amplifier.

55. The system of claim 53, wherein the signal processing circuitry includes a multiplexer.

56. The system of claim 24, wherein the sensor receives power through a wireless connection.

57. The system of claim 24, wherein the sensor transmits the multicellular signals through a wireless connection.

58. The system of claim 24, wherein the sensor includes an RF transmitter.

59. The system of claim 24, wherein the sensor includes a coil for power transmission.

60. The system of claim 24, wherein the sensor includes a coil for transmission of multicellular signals.

61. The system of claim 24, further including an external unit configured to be located external to a skull, wherein the external unit receives at least one of the multicellular signals and the processed signals.

62. The system of claim 61, wherein the external unit includes structure for communicating at least one of power and data with the sensor.

63. The system of claim 62, wherein the external unit is configured to be implanted beneath skin.

64. The system of claim 62, wherein the external unit includes a wireless communication with the sensor.

65. The system of claim 62, further comprising a power source for connection to the external unit.

66. The system of claim 24, wherein the plurality of electrodes are unbundled.

67. The system of claim 24, wherein each of the plurality of electrodes is an individual lead.

68. The system of claim 24, further comprising a calibration system for calibrating the multicellular signals.

69. The system of claim 68, wherein the calibration system is capable of being activated by a biological signal.

70. The system of claim 68, wherein the calibration system includes a set of movements for calibration.

71. The system of claim 68, wherein the calibration system includes a video monitor.

72. The system of claim 71, wherein the calibration system includes a set of movements for calibration and the video monitor is capable of displaying a selected movement.

73. The system of claim 72, wherein the calibration system is capable of correlating the selected movement with multicellular signals obtained from tracking the selected movement.

74. The system of claim 72, wherein the calibration system is capable of determining neural channel information that correlates to the selected movement.

75. The system of claim 74, wherein the calibration system is capable of transmitting the neural channel information to the interface.

76. The system of claim 72, wherein the calibration system is capable of correlating a parameter relating to the selected movement with multicellular signals obtained from tracking the selected movement.

77. The system of claim 76, wherein the parameter is a position.

78. The system of claim 76, wherein the parameter is a velocity.

79. The system of claim 76, wherein the parameter is an acceleration.

80. The system of claim 71, wherein the calibration system includes a set of movements for calibration and the video monitor is capable of displaying a simulation of a selected movement.

81. The system of claim 71, wherein the video monitor is a computer screen.

82. The system of claim 24, wherein each electrode is capable of detecting multicellular signals that include spikes of a plurality of neurons.

83. The system of claim 82, wherein the spikes of a plurality of neurons comprise a voltage signal.

84. The system of claim 83, wherein the interface is for logarithmically converting the voltage signal to obtain a converted signal.

85. The system of claim 84, wherein the interface is for electrically rectifying the converted signal to obtain a rectified signal.

86. The system of claim 85, wherein the interface is for integrating the rectified signal to obtain an integrated signal.

87. The system of claim 86, wherein the interface integrates the rectified signal over a period of time less than or equal to 100 msec.

88. The system of claim 86, wherein the interface is for smoothing the integrated signal to obtain a smoothed signal.

89. The system of claim 24, wherein the interface includes a voltage converter, an integrator, and a sample-and-hold circuit.

90. The system of claim 24, wherein the interface is for converting an analog signal that represents a multicellular signal to a digital signal.

91. The system of claim 90, wherein the interface is for transmitting the digital signal to a display system.

92. The system of claim 91, wherein the display system is a matrix of neural data channels.

93. The system of claim 90, wherein the interface is for selection of neural channels useful for control of the device.

94. The system of claim 93, wherein the interface is for processing the signals of the selected neural channels to obtain an output and transmitting the output to a controller.

95. The system of claim 93, wherein the interface is for transmitting the selected neural channels to a neural network.

96. The system of claim 95, wherein the neural network is for processing the signals of the selected neural channels to obtain an output.

97. The system of claim 96, wherein the neural network is for transmitting the output to an interface controller.

98. The system of claim 97, wherein the interface controller includes a processor for converting the output into a signal that actuates the device.

99. The system of claim 24, wherein the plurality of electrodes are configured to be placed within a brain.

100. The system of cliam 24, wherein the plurality of electrodes are configured to be placed on a surface of an extracranial site.

101. The system of claim 24, wherein an implantation site of the sensor is determined based on a pre-surgical brain imaging procedure.

102. The system of claim 101, wherein the brain imaging procedure includes using magnetic resonance imaging.

103. The system of claim 102, wherein the brain imaging procedure includes using functional magnetic resonance imaging.

104. The system of claim 24, wherein an implantation site of the sensor is an area that generates multicellular signals under a patient's voluntary control.

105. The system of claim 104, wherein the area is determined by using magnetic resonance imaging.

106. The system of claim 24, wherein the plurality of electrodes are capable of recording from clusters of neurons and outputting detected signals comprising multiple neuron signals.

107. The system of claim 24, wherein each of the plurality of electrodes is capable of detecting a plurality of neuron signals.

108. The system of claim 24, wherein the sensor is bonded to an electronic microchip including amplification circuitry.

109. The system of claim 24, wherein the sensor is capable of receiving power through a wireless connection.

110. The system of claim 24, wherein the sensor is capable of transmitting data with wireless communication.

111. The system of claim 24, wherein the interface is for converting recorded multicellular signals into a control signal for an external unit.

112. The system of claim 111, wherein the external unit is at least one of: a computer, a computer display, and a computer controlled device.

113. The system of claim 24, wherein the interface uses neural net software routines to map multicellular signals into a desired motion of an external unit.

114. The system of claim 24, wherein the interface uses at least sixteen channels of multicellular signals.

115. The system of claim 24, wherein the interface is for assigning at least one multicellular signal to a specific use.

116. The system of claim 115, wherein the specific use is determined by a patient's movement.

117. The system of claim 115, wherein the specific use is determined by a patient's attempted movement.

118. The system of claim 24, wherein the interface is for using at least one multicellular signal generated under voluntary control of a patient.

119. The system of claim 24, wherein the interface is for assigning at least one multicellular signal to motion control.

120. The system of claim 119, wherein the at least one multicellular signal is assigned to fine motion control.

121. The system of claim 24, wherein the interface is for combining multicellular signals to generate a control signal.

122. The system of claim 121, wherein the interface is for mathematically combining the multicellular signals to generate the control signal.

123. The system of claim 121, further comprising software networks for mapping multicellular signals onto desired movement functions.

124. The system of claim 24, wherein the interface is for using multicellular signals from neurons whose signals are separated from other nearby neurons.

125. The system of claim 124, wherein the interface is for separating signals by spike discriminaton methods.

126. The system of claim 24, wherein the interface is for determining a mean signal level of neural activity from one or more neurons while a patient is not attempting to generate a control signal.

127. The system of claim 126, wherein the interface is for generating a modified neural signal based on the difference between the current signal level and the mean signal level.

128. The system of claim 24, wherein the interface is for generating a control signal by summing and processing signals from ten or less neurons.

129. The system of claim 24, wherein the interface is for transmitting information from at least one specific neural channel to a neural network.

130. The system of claim 129, wherein the neural network produces a control signal.

131. The system of claim 24, wherein the interface includes a processing unit configured to be placed external to a skull.

132. The system of claim 131, wherein the processing unit is configured to be placed external to a body.

133. The system of claim 131, wherein the processing unit is configured to receive signals via a wired connection.

134. The system of claim 131, wherein the processing unit is configured to receive signals via a wireless connection.

135. The system of claim 134, wherein the processing unit is capable of having wireless communication transmissions that pass through the skull of a patient.

136. The system of claim 24, wherein the device is a prosthetic limb.

137. The system of claim 24, wherein the device is a functional electrical stimulator device.

138. The system of claim 24, wherein the device is a computer controlled device.

139. The system of claim 24, wherein the device is a teleoperated device.

140. The system of claim 24, wherein the device is configured to be turned on or off by a patient with a monitored biological signal.

141. The system of claim 140, wherein the monitored biological signal is generated by one or more of eye motion, eyelid motion, facial muscle, or other electromyographic activity.

142. The system of claim 140, wherein the monitored biological signal is a time code of brain activity.

143. The system of claim 24, wherein adaptive processing includes the performance of a calibration procedure.

144. The system of claim 143, wherein the calibration procedure is an initial calibration procedure.

145. The system of claim 143, wherein the calibration procedure is performed a plurality of times.

146. The system of claim 143, wherein the calibration procedure includes a patient attempting a task.

147. The system of claim 146, wherein the task is simulated on a video montior.

148. The system of claim 146, wherein activity on a neural channel is correlated to a selected parameter of the task.

149. The system of claim 148, wherein the neural channel is electronically routed to a control device associated with a movement parameter based on the correlation of the neural channel to the selected parameter of the task.

150. The system of claim 143, wherein the calibration procedure is performed on a periodic basis.

151. The system of claim 150, wherein the periodic basis is daily.

152. The system of claim 148, wherein the calibration procedure is initiated or ceased by the patient through a montiored biological signal.

153. The system of claim 152, wherein the monitored biological signal is generated by at least one of an eye motion, an eyelid motion, a facial muscle, and a electromyographic activity.

154. The system of claim 152, wherein the monitored biological signal is a time code of brain activity.

155. The system of claim 146, wherein a specific portion of the calibration procedure is activated independently.

156. The system of claim 155, wherein a patient assistant activates the specific portion.

157. The system of claim 155, wherein the patient, via a monitored biological signal, activates the specific portion.

158. The system of claim 24, wherein one or more channels of neural activity are routed to at least one of a control device and a movement parameter, and wherein the adaptive processing includes changing the routing over time.

159. The system of claim 158, wherein the routing changes due to fluctuating signal amplitude.

160. The system of claim 158, wherein the routing changes due to motor learning.

161. The system of claim 158, wherein the movement parameter is a position.

162. The system of claim 158, wherein the movement parameter is a velocity.

163. The system of claim 158, wherein the movement parameter is an acceleration.

164. The system of claim 24, wherein adaptive processing includes adjusting to changes in recorded signals.

165. The system of claim 164, wherein the changes are due to electrode drift.

166. The system of claim 164, wherein the changes are due to a death of cells.

167. The system of claim 164, wherein the changes are due to parameters of cell discharge.

168. The system of claim 24, wherein adaptive processing includes setting at least one of neural channel gains and other channel parameters.

169. The system of claim 168, wherein the gains are set by a prosthetic specialist after implantation of the plurality of electrodes.

170. The system of claim 24, wherein at least one of the plurality of electrodes may detect at least one neuron signal.

171. The system of claim 24, wherein the interface receives the multicellular signals from the sensor by receiving one neuron signal from one or more electrodes.

172. The device of claim 1, wherein the calibration system is capable of being activated by a biological signal.

173. The device of claim 172, wherein the calibration system includes a set of movements for calibration.

174. The device of claim 172, wherein the calibration sytem includes a video monitor.

175. The device of claim 174, wherein the calibration system includes a set of movements for calibration and the video monitor is capable of displaying a selected movement.

176. The device of claim 175, wherein the calibration system is capable of correlating the selected movement with neural signals obtained from tracking the selected movement.

177. The device of claim 175, wherein the calibration system is capable of determining neural channel information that correlates to the selected movement.

178. The device of claim 175, wherein the calibration system is capable of correlating a parameter relating to the selected movement with neural signals obtained from tracking the selected movement.

179. The device of claim 178, wherein the parameter is at least one of a position, a velocity, and an acceleration.

180. The device of claim 174, wherein the calibration system includes a set of movements for calibration and the video monitor is capable of displaying a simulation of a selected movement.

181. The device of claim 1, wherein the external unit is the external receiver.

182. The device of claim 1, wherein calibrating the collected multicellular signals with movement of the external unit includes calibrating the collected multicellular signals based on an attempt to move the external unit.

183. A device for collecting multicellular signals directly from a central nervous system of a body and transmitting the signals to an external receiver, comprising:

A) a plurality of electrodes formed in bundles of flexible wires with tips at staggered length aligned to be implanted in the central nervous system, each electrode for collecting multicellular signals from the central nervous system; and B) a signal processing mechanism connected to the electrodes for multiplexing and transmitting the signals from the electrodes to the external receiver, wherein at least a portion of the signal processing mechanism is configured to be implanted within the body and the external receiver is configured to be located external to the body and connected to the signal processing mechanism through a wireless connection;

wherein the tips of the electrodes are sized to have a recording area greater than $400\ \mu m^2$ for collecting the multicellular signals from the central nervous system.

184. The device of claim 183, wherein the signal processing mechanism receives power through the wireless connection.

185. The device of claim 183, wherein the signal processing mechanism is capable of having wireless communication transmissions that pass through a skull of a patient.

186. The device of claim 183, wherein the external receiver includes a computer.

187. The device of claim 183, wherein the external receiver includes a computer display.

188. The device of claim 183, wherein the external receiver includes an artificial limb.

189. The device of claim 183, wherein the external receiver includes a robotic component.

190. The device of claim 183, further comprising a movement calibration system for calibrating the collected multicellular signals with movement of the external receiver.

191. The device of claim 190, wherein the calibration system is capable of being activated by a biological signal.

192. The device of claim 190, wherein the calibration system includes a set of movements for calibration.

193. A device for collecting multicellular signals directly from a central nervous system and transmitting the signals to an external receiver, comprising:

A) a plurality of electrodes formed in bundles of flexible wires with tips at staggered length aligned to be implanted in the central nervous system, each electrode for collecting multicellular signals from the central nervous system; and B) a signal processing mechanism connected to the electrodes for multiplexing and transmitting the signals from the electrodes to the external receiver;

wherein the tips of the electrodes are sized to have a recording area greater than $400\ \mu m^2$ for collecting the multicellular signals from the central nervous system, wherein the external receiver is a part of a prosthetic device.

194. The device of claim 193, wherein the prosthetic device is a prosthetic limb.

195. The device of claim 193, wherein the prosthetic device incudes a robotic component.

196. The apparatus of claim 16, wherein the calibration system is capable of being activated by a biological signal.

197. The apparatus of claim 16, wherein the calibration system includes a set of movements for calibration.

198. The apparatus of claim 16, wherein the calibration system includes a video monitor.

199. The apparatus of claim 198, wherein the calibration system includes a set of movements for calibration and the video monitor is capable of displaying a selected movement.

200. The apparatus of claim 199, wherein the calibration system is capable of correlating the selected movement with neural signals obtained from tracking the selected movement.

201. The apparatus of claim 199, wherein the calibration system is capable of determining neural channel information that correlates to the selected movement.

202. The apparatus of claim 199, wherein the calibration system is capable of correlating a parameter relating to the selected movement with neural signals obtained from tracking the selected movement.

203. The apparatus of claim 202, wherein the parameter is at least one of a position, a velocity, and an acceleration.

204. The apparatus of claim 198, wherein the calibraton system includes a set of movements for calibration and the video monitor is capable of displaying a simulation of a selected movement.

205. The apparatus of claim 16, wherein the device is an enternal unit.

206. The apparatus of claim 16, wherein calibrating the collected multicellular signals with movement of the device includes calibrating the collected multicellular signals based on an attempt to move the device.

207. An apparatus for recording multi-neuron signals directly from a central nervous system of a body, comprising:
    a plurality of sensors, wherein each sensor further comprises a bundle of noble metal wires with tips at staggered lengths and with the tips sized to have a recording area greater than 400 $\mu m^2$ so that each tip collects multicellular signals from the central nervous system; and
    an interface for receiving the multicellular signals from the plurality of sensors, wherein the plurality of sensors are configured to be implanted within the body and the interface is configured to be located external to the body and connected to the sensors through a wireless connection.

208. The apparatus of claim 207, wherein the interface receives power through the wireless connection.

209. The apparatus of claim 207, wherein the interface is capable of having wireless communication transmissions that pass through a skull of the body.

210. An apparatus for recording multi-neuron signals directly from a central nervous system, comprising:
    a plurality of sensors, wherein each sensor further comprises a bundle of noble metal wires with tips at staggered lengths and with the tips sized to have a recording area greater than 400 $\mu m^2$ so that each tip collects multicellular signals from the central nervous system; and
    an interface for receiving the multicellular signals from the plurality of sensors, wherein the interface is a part of a prosthetic device.

211. The apparatus of claim 210, wherein the prosthetic device includes a prosthetic limb.

212. The apparatus of claim 210, wherein the prosthetic device includes a robotic component.

213. The system of claim 21, wherein the calibration system is capable of being activated by a biological signal.

214. The system of claim 21, wherein the calibration system includes a set of movements for calibration.

215. The system of claim 21, wherein the calibration system includes a video monitor.

216. The system of claim 215, wherein the calibration system includes a set of movements for calibration and the video monitor is capable of displaying a selected movement.

217. The system of claim 216, wherein the calibration system is capable of correlating the selected movement with neural signals obtained from tracking the selected movement.

218. The system of claim 216, wherein the calibration system is capable of determining neural channel information that correlates to the selected movement.

219. The system of claim 216, wherein the calibration system is capable of correlating a parameter relating to the selected movement with neural signals obtained from tracking the selected movement.

220. The system of claim 219, wherein the parameter is at least one of a position, a velocity, and an acceleration.

221. The system of claim 215, wherein the calibration system includes a set of movements for calibration and the video monitor is capable of displaying a simulation of a selected movement.

222. The system of claim 21, wherein the attached unit is the external receiver.

223. The system of claim 21, wherein calibrating the detected multicellular signals with movement of the attached unit includes calibrating the detected multicellular signals based on an attempt to move the attached unit.

224. A channel display system for monitoring recorded multicellular signals, comprising:
    A) a device for recording multichannel neural signals directly from a central nervous system and broadcasting the signals, wherein the device has electrodes with staggered tips, each electrode is sized to have a surface area greater than 400 $\mu m^2$, and each electrode is for detecting multicellular signals;
    B) an external receiver for receiving the multicellular signals from the device, wherein the device is configured to be implanted within a body and the external receiver is configured to be located external to the body;
    C) electric connection means for wirelessly connecting the device to the external receiver to relay the signals; and
    D) a visual dislay for displaying the signals in a matrix, wherein each cell of the matrix represents a separate neural data channel.

225. The system of claim 224, wherein the external receiver receives power through a wireless connection.

226. The system of claim 224, wherein the device is capable of having wireless communication transmissions that pass through a skull of the body.

227. A channel display system for monitoring recorded multicellular signals, comprising:
    A) a device for recording multichannel neural signals directly from a central nervous system and broadcasting the signals, wherein the device has electrodes with staggered tips, each electrode is sized to have a surface area greater than 400 $\mu m^2$, and each electrode is for detecting multicellular signals;
    B) an external receiver for receiving the multicellular signals from the device, wherein the external receiver is a part of a prosthetic device;
    C) electric connection means for connecting the device to the external receiver to relay the signals; and
    D) a visual display for displaying the signals in a matrix, wherein each cell of the matrix represents a separate neural data channel.

228. The system of claim 227, wherein the prosthetic device includes a prosthetic limb.

229. The system of claim 227, wherein the prosthetic device includes a robotic component.

230. The instrument of claim 17, wherein the external receiver includes a prosthetic device.

231. The instrument of claim 17, wherein the signal processor delivers the processed signals to muscular tissue.

232. The instrument of claim 17, wherein the sensor is for being implanted into a skull and the signal processor is located external to the skull and is coupled to the sensor through a wireless connection.

233. The instrument of claim 17, wherein the signal processor includes a neural network.

234. The instrument of claim 233, wherein the neural network comprises an artificial neural network.

235. The instrument of claim 17, wherein signal processor maps the multicellular signals onto an output parameter and the signal processor comprises a neural network.

236. The instrument of claim 17, wherein the signal processor shapes the processed signal for control of a prosthetic device, wherein the signal processor comprises a neural network.

237. The instrument of claim 236, wherein the signal processor further includes a controller for receiving an output of the neural network.

238. The instrument of claim 17, further including a movement calibration system for calibrating the received multicellular signals with movement of a prosthetic device.

239. The instrument of claim 238, wherein the calibration system is capable of being activated by a biological signal.

240. The instrument of claim 239, wherein the calibration system includes a set of movements for calibration.

241. The instrument of claim 240, wherein the calibration system includes a video monitor that is capable of displaying a selected movement.

242. The instrument of claim 241, wherein the calibration system is capable of correlating the selected movement with neural signals obtained from tracking the selected movement.

243. The system of claim 24, wherein the device includes the external unit.

* * * * *